US010646430B2

(12) United States Patent
Wenzel et al.

(10) Patent No.: US 10,646,430 B2
(45) Date of Patent: May 12, 2020

(54) TOPICAL COMPOSITIONS FOR STIMULATING ADIPOGENESIS AND LIPOGENESIS TO REDUCE THE SIGNS OF SKIN AGING

(71) Applicant: Kimberly-Clark Worldwide, Inc., Neenah, WI (US)

(72) Inventors: Scott W. Wenzel, Neenah, WI (US); David J. Tyrrell, Milwaukee, WI (US); Alencia Vanay Grice, Roswell, GA (US); Stephanie VandeVen Teat, Roswell, GA (US); Jeffery Richard Seidling, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 436 days.

(21) Appl. No.: 15/306,356

(22) PCT Filed: Apr. 30, 2014

(86) PCT No.: PCT/US2014/036233
§ 371 (c)(1),
(2) Date: Oct. 24, 2016

(87) PCT Pub. No.: WO2015/167557
PCT Pub. Date: Nov. 5, 2015

(65) Prior Publication Data
US 2017/0042796 A1 Feb. 16, 2017

(51) Int. Cl.
| A61K 36/03 | (2006.01) |
| A61K 36/28 | (2006.01) |
| A61K 8/97 | (2017.01) |
| A61Q 19/08 | (2006.01) |
| A61Q 19/00 | (2006.01) |
| A61K 8/9706 | (2017.01) |
| A61K 8/63 | (2006.01) |

(52) U.S. Cl.
CPC .................. *A61K 8/97* (2013.01); *A61K 8/63* (2013.01); *A61K 8/9706* (2017.08); *A61Q 19/005* (2013.01); *A61Q 19/007* (2013.01); *A61Q 19/08* (2013.01); *A61K 2800/596* (2013.01); *A61K 2800/74* (2013.01)

(58) Field of Classification Search
CPC ................................ A61K 36/03; A61K 36/28
USPC ............................................. 424/195.18, 764
See application file for complete search history.

(56) References Cited

U.S. PATENT DOCUMENTS

| 3,296,145 A | 1/1967 | Findlan et al. |
| 5,387,208 A | 2/1995 | Ashton et al. |
| 5,804,206 A | 9/1998 | D'Amelio et al. |
| 5,925,615 A | 7/1999 | Kern et al. |
| 5,939,078 A | 8/1999 | Fujimura et al. |
| 5,955,407 A | 9/1999 | Davister et al. |
| 6,613,030 B1 | 9/2003 | Coles et al. |
| 6,616,922 B2 | 9/2003 | Taylor et al. |
| 7,842,232 B2 | 11/2010 | Bosch et al. |
| 8,101,211 B2 | 1/2012 | Chiba et al. |
| 8,496,948 B2 | 7/2013 | Harripersad |
| 8,568,752 B2 | 10/2013 | Schultz |
| 8,580,741 B2 | 11/2013 | Lee et al. |
| 2001/0044393 A1 | 11/2001 | Peterson, Jr. et al. |
| 2002/0028227 A1 | 3/2002 | Yu et al. |
| 2002/0098218 A1 | 7/2002 | Zhuang et al. |
| 2003/0021850 A1 | 1/2003 | Xu |
| 2003/0185869 A1 | 10/2003 | Wertz et al. |
| 2003/0190337 A1 | 10/2003 | Bissett |
| 2004/0028643 A1 | 2/2004 | Chiba et al. |
| 2005/0048008 A1 | 3/2005 | Gupta |
| 2007/0179207 A1 | 8/2007 | Fernandez de Castro et al. |
| 2007/0248563 A1 | 10/2007 | Iovanni et al. |
| 2007/0292461 A1 | 12/2007 | Tamarkin et al. |
| 2008/0112968 A1 | 5/2008 | Gebicki |
| 2008/0241070 A1 | 10/2008 | Ryde et al. |
| 2009/0012049 A1 | 1/2009 | Fabre et al. |
| 2009/0318322 A1 | 12/2009 | Taylor et al. |
| 2010/0099640 A1 | 4/2010 | Geuns et al. |
| 2011/0086088 A1 | 4/2011 | Berry |
| 2011/0129453 A1 | 6/2011 | Harripersad |
| 2011/0144214 A1 | 6/2011 | Snyder et al. |
| 2011/0262505 A1 | 10/2011 | Athwal |
| 2012/0070341 A1 | 3/2012 | Eder et al. |
| 2012/0107427 A1 | 5/2012 | Kim et al. |
| 2013/0017239 A1 | 1/2013 | Viladot Petit et al. |
| 2013/0059929 A1 | 3/2013 | Koehler et al. |

FOREIGN PATENT DOCUMENTS

| BR | PI1003665 A2 * | 3/2012 | |
| BR | PI1003665 A2 | 3/2012 | |
| CN | 101621984 A | 1/2010 | |
| DE | 202012005442 U1 * | 7/2012 | ............. A61K 8/735 |

(Continued)

OTHER PUBLICATIONS

Derwent Abstract of BR 201003665 A2, retrieved on Jan. 15, 2019, 2 pages.
Koster et al., "Rwandan female genital modification: Elongation of the Labia Minora and the use of local botanical species", Culture, Health & Sexuality, vol. 10, No. 2, pp. 191-204.
Chemyunion: Richesses D'Amazonie, Parfums Cosmetiques Actualites, "The Wealth of the Amazon", Sep. 2009, KOSMET database Abstract, 1 page.

(Continued)

*Primary Examiner* — Michael Barker
*Assistant Examiner* — Deborah A Davis
(74) *Attorney, Agent, or Firm* — Armstrong Teasdale LLP

(57) ABSTRACT

Compositions for reducing skin aging are disclosed herein. The compositions can be topically applied to a skin region to reduce or prevent skin wrinkles, fine lines, thinning skin, sagging skin, skin dryness, and skin itchiness.

20 Claims, 10 Drawing Sheets

(56) References Cited

FOREIGN PATENT DOCUMENTS

| | | | |
|---|---|---|---|
| DE | 202012005442 U1 | 7/2012 | |
| EP | 0965323 A2 | 12/1999 | |
| EP | 1649873 A2 | 4/2006 | |
| JP | 11269036 A | 10/1999 | |
| JP | 2001335422 A | * 12/2001 | ............. A61K 7/00 |
| JP | 2004083442 A | 3/2004 | |
| JP | 4073358 B2 | 11/2004 | |
| JP | 2004323362 A | 11/2004 | |
| JP | 2009057290 A | 3/2009 | |
| KR | 20090005839 A | 1/2009 | |
| KR | 2013106712 A | 9/2013 | |
| KR | 1020140036400 A | 4/2014 | |
| WO | 0126595 A1 | 4/2001 | |
| WO | 02087645 A1 | 11/2002 | |
| WO | 03018732 A1 | 3/2003 | |
| WO | 2005047445 A1 | 5/2005 | |
| WO | 2008096203 A2 | 8/2008 | |
| WO | 2009098476 A1 | 8/2009 | |
| WO | 2009109869 A2 | 9/2009 | |
| WO | 2010039291 A1 | 4/2010 | |
| WO | 2010127231 A2 | 11/2010 | |
| WO | 2011124241 A2 | 10/2011 | |
| WO | 2012145609 A1 | 10/2012 | |

OTHER PUBLICATIONS

Hu et al., "Antioxidant activity of sulfated polysaccharide fractions extracted from Undaria pinnitafida in vitro", International Journal of Biological Macromolecules, Mar. 1, 2010, vol. 46, No. 2, pp. 193-198.
Hyun, Y. J., "Photoprotective effect of Undaria crenata against ultraviolet B-induced damage to keratinocytes", Journal of Bioscience and Bioengineering, Mar. 6, 2013, vol. 116, No. 2, pp. 256-264.
Kim et al., "Fucoidan from the sporophyll of Undaria pinnatifida suppresses adipocyte differentiation by inhibition of inflammation-related cytokines in 3T3-L1 cells", Nutrition Research, May 18, 2012, vol. 32, No. 6, pp. 439-447.
Yang et al., "Protection from oxidative damage using Bidens pilosa extracts in normal human erythrocytes", Food and Chemical Toxicology, Sep. 2006, vol. 44, No. 9, pp. 1513-1521.
International Search Report and Written Opinion for International Application No. PCT/US2014/036199, dated Feb. 29, 2016, 10 pages.
International Preliminary Report on Patentability for International Patent Application No. PCT/US14/36199, dated Jul. 15, 2016, 7 pages.
International Search Report and Written Opinion for International Application No. PCT/US2014/036206, dated Jan. 29, 2015, 12 pages.
International Preliminary Report on Patentability for International Patent Application No. PCT/US2014/036206, dated Apr. 25, 2016, 5 pages.
International Search Report and Written Opinion for International Application No. PCT/US2014/036210, dated Jan. 15, 2015, 12 pages.
International Preliminary Report on Patentability for International Patent Application No. PCT/US2014/036210, dated Jul. 11, 2016, 6 pages.
International Search Report and Written Opinion for International Application No. PCT/US2014/036216, dated Jan. 15, 2015, 14 pages.
International Preliminary Report on Patentability for International Patent Application No. PCT/US2014/036216, dated Apr. 7, 2016, 7 pages.
International Search Report and Written Opinion for International Application No. PCT/US2014/036223, dated Jan. 29, 2015, 9 pages.
International Preliminary Report on Patentability for International Patent Application No. PCT/US2014/036223, dated Apr. 28, 2016, 5 pages.
International Search Report and Written Opinion for International Application No. PCT/US2014/036233, dated Jan. 28, 2015, 14 pages.
International Preliminary Report on Patentability for International Patent Application No. PCT/US2014/036233, dated Apr. 29, 2016, 6 pages.
International Search Report and Written Opinion for International Application No. PCT/US2014/036242, dated Jan. 15, 2015, 13 pages.
International Preliminary Report on Patentability for International Patent Application No. PCT/US2014/036242, dated Apr. 12, 2016, 5 pages.
Office Action issued in GB 1618949.0, dated Feb. 6, 2018, 6 pages.
Science in Nature, Chemyunion Quimica LTDA, http://www.incosmetics.com/_novadocuments/9242, 6 pages.
Pandel et al., "Skin Photoaging and the Role of Antioxidants in Its Prevention", ISRN Dermatology, 2013, vol. 2013, Article ID 930164, 11 pages.

* cited by examiner

Negative Control

Positive Control

Adipofill'in

Ecobidens

Ecosamba

Kombuchka

Negative Control

Positive Control

Adipofill'in

Ecobidens

Ecosamba

Kombuchka

Undarine – Undaria pinnatifida (Barnet)

Wakamine – Undaria pinnatifida

Maritech Glycomix – Undaria pinnatifida

Maritech Reverse – Undaria pinnatifida

Negative Control

Positive Control

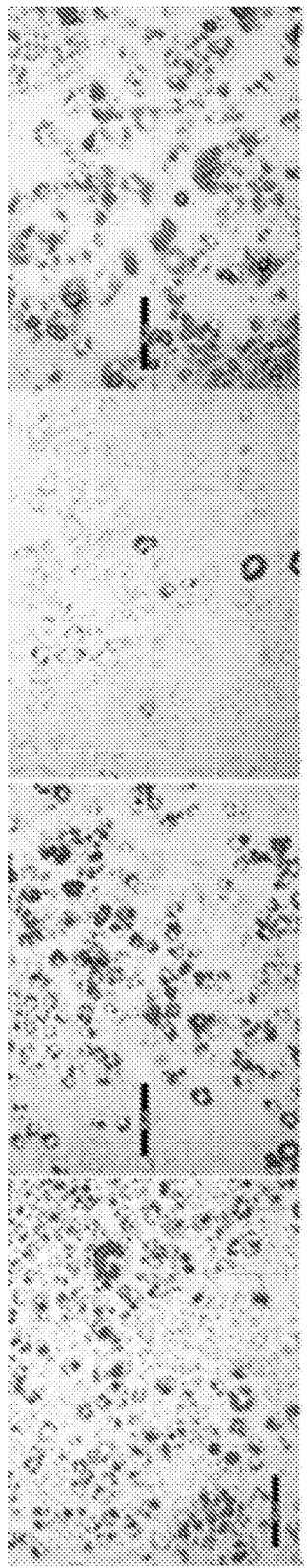
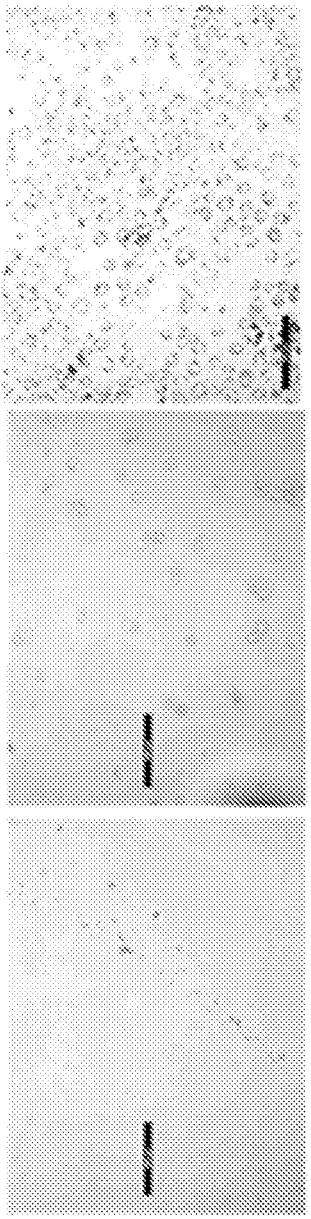
FIG. 7A Sym3D 1% w/v
FIG. 7B Volufiline 1%
FIG. 7C Commipheroline 1%
FIG. 7D Biobustyl 1%
FIG. 7E Cellactive Form 1%
FIG. 7F Adifyline 1%
FIG. 7G Voluform 1%

Ecobidens – Bidens pilosa (ChemyUnion)

Bidens pilosa (Carrubba)

Bidens tripartita (Provital)

Bidens bipinnata (Carrubba)

Negative Control

Positive Control

TOPICAL COMPOSITIONS FOR STIMULATING ADIPOGENESIS AND LIPOGENESIS TO REDUCE THE SIGNS OF SKIN AGING

BACKGROUND OF THE DISCLOSURE

The present disclosure relates generally to compositions and methods to reduce the signs of skin aging of the face and body. More particularly, the present disclosure relates to compositions including an *Undaria* extract and/or *Bidens* extract and methods of topically applying the compositions for stimulating adipogenesis and lipogenesis to reduce signs of skin aging.

Human skin changes drastically with age, becoming thinner and drier due to thinning of the epithelial layer and degeneration of underlying fat and connective tissue. Other signs of aged skin include loss of skin elasticity, firmness and resiliency.

The skin of the face and neck areas are particularly prone to signs of aging. Signs of aging that affect the skin of the face and neck include, for example, wrinkles, fine lines, thinning skin, sagging skin, skin dryness and skin itchiness.

Changes in hormonal status (e.g., decrease in estrogen levels, increase in follicle-stimulating hormone (FSH) levels) during perimenopause and menopause can make changes in the skin even more pronounced. Atrophic manifestations associated with menopause such as skin thinning and the accompanying functional decrease in skin "strength" are systemic. In particular, there is a marked decrease in collagen I and collagen III and a decrease in size and number of adipocytes in aged skin. These effects result in skin areas, and in particular, facial skin, neck skin, chest skin, breast skin, hand skin, leg skin, and feet skin, showing increased signs of aging (e.g., wrinkles, fine lines, sagging skin, thinning skin, etc.).

Vulvar skin and the labia are particular additional skin regions that change as a woman ages, especially as a result of the changes in hormone levels during and following menopause. Vulvar skin and the labia can lose elasticity as a result of the degeneration of underlying fat and connective tissues, loss of collagen and thinning of the epithelial layer of the skin. The vulvar skin can also become less moist. The loss of elasticity and moisture of the mucosal vulvar skin can diminish the youthful look of the vulvar anatomy. A woman can become ashamed and even depressed about the toll that aging takes on the appearance of her outer genitalia as a result of changes of the vulvar skin and labia.

A wide variety of creams and lotions exist that can cosmetically improve the appearance, and sometimes, the structure of the skin on the face and body. Such compositions often employ retinoids, hydroxy acids and/or exfoliants to encourage skin rejuvenation, increase firmness or otherwise cosmetically improve the skin. Many cosmetic products provide moisture and can enhance the skin's appearance by plumping the skin using irritants that cause inflammation. Further, there are known active cosmetic ingredients that claim to enhance adipogenesis, however, their potency is variable and therefore has not been shown to be effective for this use. Other cosmetic products are available that claim to rejuvenate and create a more youthful appearance by targeting extracellular matrix proteins such as elastin and collagen, which are produced by fibroblasts. These compositions can be inappropriate for use on the delicate mucous membrane of the vulva and labia. Incompatibility with mucosal skin necessitates alternative cosmetic creams and lotions specifically designed for application to reduce the effects of aging of the vulvar skin and labia.

Medical procedures, such as dermal injections and reconstructive surgery, are also available to reduce the signs of aging. Cosmetic surgery has recently grown in popularity to aesthetically enhance the appearance of skin and even the appearance of the skin of the vulva and labia. These procedures, however, are not always desirable options as surgery can be costly, painful and very invasive.

While the cosmetic products and medical procedures described above are suitable for treating aged skin of the face and body and aging of the vulvar skin and labia, alternative compositions and methods for improving skin are desirable. Accordingly, there exists a need to develop alternative compositions and methods for improving the overall fullness and appearance of aging skin of the face and body and aging of the vulvar skin and labia. It would be highly advantageous if the compositions and methods could be topically applied such that invasive, painful, and costly medical procedures could be avoided.

BRIEF DESCRIPTION OF THE DISCLOSURE

The present disclosure is generally directed to compositions and methods to reduce the signs of skin aging. In one aspect, the present disclosure is directed to a topical composition comprising an *Undaria* extract, a *Bidens* extract, and a hydrophilic carrier.

In another aspect, the present disclosure is directed to a topical composition comprising an *Undaria* extract, a *Bidens* extract selected from the group consisting of *Bidens pilosa* extract, *Bidens bipinnata* extract, *Bidens tripartita* extract and combinations thereof, a skin penetration enhancer, and a hydrophilic carrier.

In yet another aspect, the present disclosure is directed to a topical composition comprising an *Undaria pinnatifida* extract, a *Bidens pilosa* extract, glycerin, and a hydrophilic carrier.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 7A-7G are photomicrographs of mouse 3T3-1L cells stained with Oil Red-O following treatment with additional active ingredients, as discussed in Example 6.

Figure 1:
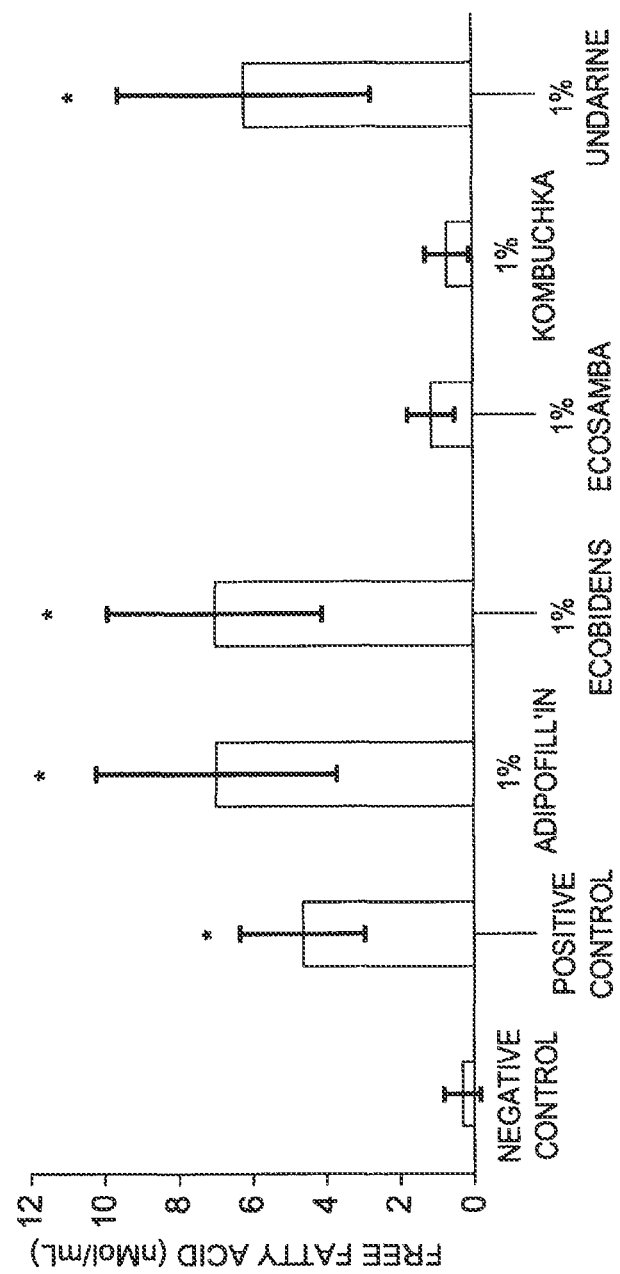
FIG. 1 is a graphical illustration showing free fatty acid production after treatment of cells with various active ingredients, as discussed in Example 1. *$P<0.05$ by Student's T test to negative control, N=4. Data represents mean with standard deviation.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure, compositions and methods have been discovered that surprisingly allow for reducing the signs of skin aging. The methods of the present disclosure have a broad and significant impact, as they increase adipocyte size and number ("adipogenesis") and lipid production ("lipogenesis") to result in a more youthful appearance of aged skin of the face and body. More particularly, as used herein, the term "adipogenesis" refers to increased proliferation of adipocytes and/or increased differentiation of adipose-derived stem cells. Increasing adipocyte cell number and/or lipid production within adipocytes can reduce the signs of skin aging, including counteracting skin thinning, increasing overall fullness, increasing skin firmness and increasing skin resiliency.

As used herein, "body" refers to an individual's entire body, and particularly, includes the regions of the face (including forehead, cheeks, chin, and eyelids), neck, shoulders, breast, chest, legs, hands, feet and vulvar area including vulvar skin, for example, the vulva, labia, labia majora, labia minor, mons pubis, vulval vestibule, and combinations thereof.

Compositions
Active Ingredients/Extracts

The present disclosure has unexpectedly found that particular extracts can be topically applied, alone or in combination, to an individual's skin as active ingredients in compositions to reduce the signs of skin aging. Particularly, while the active ingredients of the compositions have been previously known to stimulate collagen and elastin, it has now been unexpectedly found that these active ingredients increase adipogenesis and/or lipogenesis, thereby increasing the number and size of adipocytes in subcutaneous adipose tissue found directly below the skin. This provides the user with plumper, fuller skin and a more youthful, smoother skin appearance.

*Undaria* Extract

In one aspect, the present disclosure is directed to compositions for reducing the signs of skin aging of the face and body; the compositions generally include an *Undaria* extract as the active ingredient. As used herein, "extract" refers to the active solid components from the *Undaria* plant.

An *Undaria* extract is an extract obtained from *Undaria*, a genus of brown alga that includes *U. crenata, U. peterseniana, U. pinnatifida* and *U. undarioides*. As stated above, *Undaria* extracts are known to stimulate collagen and elastin, and have specifically been described in vendor literature to increase 14 genes linked to collagen and elastin production.

*Undaria* spp. are brown algae plants that contain fucoidan in the cells walls. As used herein, *Undaria* extract, refers to a liquid extract from the *Undaria* plant, however, does not include an extract that has been further supplemented/ standardized for fucoidan content. Particularly, the *Undaria* extracts for use in the topical compositions of the present disclosure include extracts obtained by soaking or passing the *Undaria* algae plants in/over water with no further chemical treatment. The soaking/passing over can be accomplished with any method known in the extraction arts, such as, for example, lixiviation, infusion steeping, percolation, extraction, and the like, and combinations thereof. In some embodiments, the *Undaria* plant could be mascerated to further obtain the extract. Additionally, the water used in these processes could be heated to obtain the *Undaria* extract.

One particularly suitable method for obtaining the *Undaria* extract is lixiviation of fertile bases from lyophilized *Undaria* algae plants. As used herein, "lixiviation" refers to a technique where water is slowly passed over a solid (here, *Undaria*) in a layer of varying depth to extract soluble material. The general technique is described in FR 2693917, which is incorporated herein to the extent it is consistent herewith, and is performed at room temperature. After removal of the extract, in some embodiments, the extract is further diluted with diluents including water, glycerin, propanediol, butylene glycol, propylene glycol and combinations thereof.

By contrast, *Undaria* extracts that are supplemented/ standardized for fucoidan content typically are obtained by an extraction procedure utilizing an acid/water mixture having a pH of between 0 and 2, preferably between about 0 and 1, at temperatures between about 0 and 30° C., preferably between about 15 and 25° C.

Fucoidan has been shown in literature to inhibit adipogenesis (Kim, K. J. et al., "Fucoidan from the sporophyll of *Undaria pinnatifida* suppresses adipocyte differentiation by inhibition of inflammation-related cytokines in 3T3-L1 cells," Nutr. Res. 32(6): 439-447). Further, as shown in the Examples below, MARITECH® REVERSE (Cambridge, Australia), which is standardized to at least 85% fucoidan, did not increase adipogenesis and lipogenesis. As disclosed herein, however, the *Undaria* extracts used in the compositions of the present disclosure, which are of the same species known to contain fucoidan, surprisingly and unexpectedly resulted in an increase in adipogenesis and lipogenesis.

Suitable *Undaria* extracts can be obtained from commercially available sources (e.g., Barnet Products Corp., Englewood Cliffs, N.J.; Changsha Organic Herb Inc., Hunan, China). A particularly suitable commercially available formulation including *Undaria* extract can be, for example, UNDARINE™, which is a formulation including glycerin, water and *U. pinnatifida* extract (commercially available from Barnet Products Corp., Englewood Cliffs, N.J.).

Another suitable commercially available *Undaria* extract can be, for example, the *U. pinnatifida* extract WAKAMINE® (INCI: water (and) *Undaria pinnatifida* extract), commercially available from SOLIANCE (France), which has previously been used to lighten skin and prevent age-spots.

Suitable amounts of an *Undaria* extract for use in the topical compositions can be from about 0.01% (w/w) to about 10% (w/w), from about 0.05% (w/w) to about 7.5% (w/w), from about 0.1% (w/w) to about 5% (w/w), and from about 1% (w/w) to about 5% (w/w). As used herein "w/w" refers to the amount of the component "by weight of the composition".

*Bidens* Extract

In another aspect, the present disclosure is directed to a composition including a *Bidens* extract as the active ingredient. As used herein, "extract" refers to the active solid components from the *Bidens* plant. *Bidens* is a genus of plants in the Asteraceae family that includes many species members. *Bidens* is known to increase collagen and elastin production. Surprisingly and unexpectedly, as disclosed herein, *Bidens* extract has been found to increase adipogenesis and lipogenesis.

Suitable *Bidens* extracts include extracts of *Bidens alba, Bidens amplectens, Bidens amplissima, Bidens aristosa, Bidens asymmetrica, Bidens aurea, Bidens beckii, Bidens bidentoides, Bidens bigelovii, Bidens bipinnata, Bidens biternata, Bidens campylotheca, Bidens cernua, Bidens cervicata, Bidens chippii, Bidens conjuncta, Bidens connata, Bidens coronata, Bidens cosmoides, Bidens cynapiifolia, Bidens discoidea, Bidens eatonii, Bidens ferulifolia, Bidens forbesii, Bidens frondosa, Bidens gardneri, Bidens hawaiensis, Bidens henryi, Bidens heterodoxa, Bidens heterosperma, Bidens hillebrandiana, Bidens hyperborean, Bidens laevis, Bidens lemmonii, Bidens leptocephala, Bidens leptophylla, Bidens macrocarpa, Bidens mannii, Bidens mauiensis, Bidens maximowicziana, Bidens menziesii, Bidens micrantha, Bidens mitis, Bidens molokaiensis, Bidens x multticeps, Bidens parviflora, Bidens pilosa, Bidens polylepis, Bidens populifolia, Bidens radiate, Bidens reptans, Bidens sandvicensis, Bidens schimperi, Bidens simplicifolia, Bidens socorrensis, Bidens squarrosa, Bidens subalternans, Bidens tenuisecta, Bidens torta, Bidens trichosperma, Bidens triparfita, Bidens triplinervia, Bidens valida, Bidens vulgata, Bidens wiebkei*, and combinations thereof.

Particularly suitable *Bidens* extracts can be, for example, *Bidens pilosa* extract, *Bidens bipinnata* extract, and *Bidens tripartita* extract. Suitable *Bidens* extract can be obtained from commercially available sources (e.g., Chemyunion Quimica Ltd., Sao Paulo, Brazil; and Carrubba Inc., Milford, Conn.). Suitable *Bidens* extracts can also include *Bidens* extract blends with hydrophilic carriers such as for example, water, glycerin, propanediol, butylene glycol, propylene glycol and combinations thereof and *Bidens* extract blends with hydrophobic carriers such as for example natural oils, synthetic oils and combinations thereof. A particularly suitable *Bidens* extract can be, for example, ECOBIDENS™ (commercially available from Chemyunion Quimica Ltd., Sao Paulo, Brazil). ECOBIDENS™ is a glycerin extract of *Bidens pilosa* L. Other commercially available *Bidens* extracts include, for example, Water Agrimony Extract H.G., a *B. tripartita* extract from Provital Group (Spain); *Bidens* Extract M9983-WS, a *B. pilosa* extract, and *Bidens bipinnata* Extract N0061-WS, a *B. bipinnata* extract, both available from Carrubba Inc. (Milford, Conn.).

Suitable amounts of *Bidens* extract in the topical compositions can be from about 0.01% (w/w) to about 10% (w/w), from about 0.05% (w/w) to about 7.5% (w/w), from about 0.1% (w/w) to about 5% (w/w), and from about 1% (w/w) to about 5% (w/w).

*Undaria* Extract and *Bidens* Extract

In some particularly suitable aspects, the present disclosure is directed to a composition including a combination of the active ingredients of an *Undaria* extract and a *Bidens* extract.

When used in a combination, suitable amounts of the *Undaria* extract in the topical compositions can be from about 0.01% (w/w) to about 20% (w/w), from about 0.05% (w/w) to about 15% (w/w), and from about 0.1% (w/w) to about 10% (w/w). Suitable amounts of *Bidens* extract in the topical compositions can be from about 0.01% (w/w) to about 20% (w/w), from about 0.05% (w/w) to about 15% (w/w), from about 0.1% (w/w) to about 10% (w/w), from about 0.1% (w/w) to about 5% (w/w), and from about 1% (w/w) to about 5% (w/w).

Additional Optional Ingredients

The compositions described herein can further include additional ingredients and optional ingredients.

Generally, the compositions include a carrier with the active ingredient(s).

In one embodiment, for example, when the topical composition is to be applied to the vulvar region of an individual, the composition includes the active ingredient(s) and a hydrophilic carrier, a hydrophilic thickener, and/or a penetration enhancer. Suitable hydrophilic carriers can be, for example, water, alcohols, glycerin, glycerin derivatives, glycols, water-soluble emollients, and combinations thereof. Suitable examples of alcohols could include, but are not to be limited to, ethanol and isopropyl alcohol. Suitable examples of glycerin derivatives could include, but are not to be limited to, PEG-7 glyceryl cocoate. Suitable glycols could include, but are not to be limited to, propylene glycol, butylene glycol, pentylene glycol, ethoxydiglycol, dipropylene glycol, propanediol, and PEG-8. Suitable examples of water-soluble emollients could include, but are not to be limited to, PEG-6 Caprylic Capric Glycerides, Hydrolyzed Jojoba Esters, and PEG-10 Sunflower Glycerides.

In particularly suitable embodiments, the topical compositions are liquid compositions desirably containing water as the carrier. Suitable amounts of water can be from about 0.1% by weight of the composition to about 99.9% by weight of the composition. More typically, the amount of water can be from about 40% by weight of the composition to about 99.9% by weight of the composition. Preferably, the amount of water can be from about 60% by weight of the composition to about 99.9% by weight of the composition.

In another embodiment, the composition includes the active ingredient(s) and a hydrophobic carrier. Suitable hydrophobic carriers can be, for example, natural oils, synthetic oils and combinations thereof.

The topical compositions described herein can further include a skin penetrating enhancer or a mixture of skin penetration enhancers. A skin penetrating enhancer allows for the composition to pass through the epidermal layer and the dermal layer of the skin to reach the adipose tissue that underlies the skin wherein adipocytes are increased in number and/or size. This may be accomplished by a number of different mechanisms including, for example, by extracting lipids from the stratum corneum, increasing the partitioning of the *Undaria* and *Bidens* into the skin, and disrupting the lipid bilayer of the stratum corneum, thus rendering the stratum corneum structure more fluid and increasing the ability of the *Undaria* and *Bidens* to diffuse through the stratum corneum.

Examples of suitable skin penetration enhancers include sulfoxides, alcohols, fatty acids, fatty acid esters, polyols, amides, surfactants, terpenes, alkanones, and organic acids, among others. Specific examples of suitable sulfoxides include dimethylsulfoxide (DMSO) and decylmethylsulfoxide, among others. Suitable alcohols include alkanols such as ethanol, propanol, butanol, pentanol, hexanol, octanol, n-octanol, nonanol, decanol, 2-butanol, 2-pentanol, and benzyl alcohol; fatty alcohols, such as caprylic alcohol, decyl alcohol, lauryl alcohol, 2-lauryl alcohol, myristyl alcohol, cetyl alcohol, stearyl alcohol, oleyl alcohol, linoleyl alcohol, and linolenyl alcohol; and isopropyl alcohol. Examples of suitable fatty acids include linear fatty acids such as valeric acid, heptanoic acid, pelagonic acid, caproic acid, capric acid, lauric acid, myristic acid, stearic acid, oleic acid, and caprylic acid; and branched fatty acids, such as isovaleric acid, neopentanoic acid, neoheptanoic acid, neononanoic acid, trimethyl hexanoic acid, neodecanoic acid, and isostearic acid. Examples of suitable fatty acid esters include aliphatic fatty acid esters such as isopropyl n-butyrate, isopropyl n-hexanoate, isopropyl n-decanoate, isopropyl myristate, isopropyl palmitate, and octyldodecyl myristate; alkyl fatty acid esters such as ethyl acetate, butyl acetate, methyl acetate, methylvalerate, methylpropionate, diethyl sebacate, and ethyl oleate; and diisopropyl adipate and dimethyl isosorbide. Examples of suitable polyols include propylene glycol, butylene glycol, polyethylene glycol, ethylene glycol, diethylene glycol, triethylene glycol, dipropylene glycol, ethoxydiglycol, pentylene glycol, glycerol, propanediol, butanediol, pentanediol, hexanetriol, and glycerin. Examples of suitable amides include urea, dimethylacetamide, diethyltoluamide, dimethylformamide (DMF), dimethyloctamide, dimethyldecamide, biodegradable cyclic urea (e.g., 1-alkyl-4-imidazoline-2-one), pyrrolidone derivatives, biodegradable pyrrolidone derivatives (e.g., fatty acid esters of N-(2-hydroxyethyl)-2-pyrrolidone), cyclic amides, hexamethylenelauramide and its derivatives, diethanolamine, and triethanolamine. Examples of pyrrolidone derivatives include 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-methyl-4-methoxycarbonyl-2-pyrrolidone, 1-hexyl-4-methoxycarbonyl-2-pyrrolidone, 1-lauryl-4-methoxycarbonyl-2-pyrrolidone, N-cyclohexylpyrrolidone, N-dimethylaminopropylpyrrolidone, N-cocoalkypyrrolidone, N-tallowalkylpyrrolidone, and N-methylpyrrolidone. Examples of cyclic amides include 1-dodecylazacycloheptane-2-one (e.g., Azone®), 1-geranylazacycloheptan-2-one, 1-farnesylazacycloheptan-2-one, 1-geranylgeranylazacycloheptan-2-one, 1-(3,7-dimethyloctyl)azacycloheptan-2-one, 1-(3,7,11-trimethyldodecyl)azacyclohaptane-2-one, 1-geranylazacyclohexane-2-one, 1-geranylazacyclopentan-2,5-dione, and 1-farnesylazacyclopentan-2-one.

Typically, the compositions of the present disclosure include from about 0.01% (by weight of the composition) to about 25% (by weight of the composition) of a skin penetration enhancer, including from about 1% (by weight of the composition) to about 15% (by weight of the composition) of a skin penetration enhancer, and including from about 2% (by weight of the composition) to about 10% (by weight of the composition) of a skin penetration enhancer.

Optionally, the *Undaria* and/or *Bidens*-containing topical compositions may be formulated with a polar co-solvent to further increase the permeability of the *Undaria* and *Bidens* into the skin. Preferably, the polar co-solvent is fully miscible in the composition, and has a high affinity for the intercellular spaces in the stratum corneum. Without wishing to be bound by any particular theory, it is believed that polar co-solvents with such characteristics are driven by osmosis into the intercellular spaces in the stratum corneum, causing the stratum corneum to swell. In such a swollen state, the intercellular spaces are more liquid-like and disordered, which enables the *Undaria* and/or *Bidens* extracts to more easily diffuse through the stratum corneum.

Examples of suitable polar co-solvents for inclusion in the compositions of the present disclosure include glycerin, propanediol, ethanol, propylene glycol, butanol, isopropanol, propanol, dimethyl isosorbide, butylene glycol, polyethylene glycol, dipropylene glycol, ethoxydiglycol, pentylene glycol, and combinations thereof.

Typically, the compositions of the present disclosure include from about 1% (by weight of the composition) to about 99% (by weight of the composition) of a polar co-solvent, including from about 1% (by weight of the composition) to about 75% (by weight of the composition) of a polar co-solvent, including from about 1% (by weight of the composition) to about 50% (by weight of the composition) of a polar co-solvent, including from about 1.5% (by weight of the composition) to about 25% (by weight of the composition) of a polar co-solvent, including from about 2% (by weight of the composition) to about 15% (by weight of the composition) of a polar co-solvent, and including from about 2.5% (by weight of the composition) to about 10% (by weight of the composition) of a polar co-solvent.

In some embodiments, the compositions can further include beta-sitosterol. It is believed that in combination with *Undaria* and/or *Bidens* extract, beta-sitosterol further reduces signs of skin aging of the face and body by stimulating adipogenesis and lipogenesis, and further stimulating collagen, elastin and extracellular matrix production.

Suitable amounts of beta-sitosterol can be from about 0.001% by weight of the composition to about 10.0% by weight of the composition. More typically, the amount of beta-sitosterol can be from about 0.005% by weight of the composition to about 7.5% by weight of the composition. Even more suitable, the amount of beta-sitosterol can be from about 0.01% by weight of the composition to about 5.0% by weight of the composition.

The composition can further include other known collagen, elastin, and extracellular matrix-stimulating ingredients. Collagen is a protein found in the connective tissue of the skin and other tissues of the body. Suitable collagen enhancers can be, for example, vitamins such as ascorbic acid and derivatives thereof, peptides such as palmitoyl tripeptide-5, botanical extracts such as pomegranate or mushroom, and minerals such as hematite.

Elastin is a protein found in the connective tissue of the skin and other tissues of the body. Suitable elastin enhancers can be, for example, vitamins such as ascorbic acid and derivatives thereof, peptides such palmitoyl hexapeptide-12, botanical extracts such as kudzu, horsetail, rice, dill and rosemary, and minerals such as zinc and copper.

The compositions can further include a vasodilator. Vasodilators can increase the blood flow within the skin. Suitable vasodilators can be, for example, glyceryl trinitrate, resveratrol, caffeine, ginger extract, ginseng and other botanical extracts such as, for example, hawthorn, mint, ivy, coffee and tea.

The compositions can further include a skin soothing agent. As used herein, "skin soothing agent" refers to compounds that reduce or prevent skin irritation. Skin irritation can result from loss of moisture, a change in pH, sweat, contact dermatitis from perfumes, powders, laundry detergent from clothing, and other compounds. Skin soothing agents can reduce irritation by neutralizing an irritant, down-regulating inflammatory cascades in the skin, and/or providing a protective layer on the skin. Suitable skin soothing agents can be, for example, botanical extracts such as calendula, chamomile, aloe, comfrey, coneflower; active materials such as allantoin, bisabolol, panthenol, beta-glucan, colloidal oatmeal, and ingredient blends such as SYMCALMIN (INCI: butylene glycol, pentylene glycol, hydroxyphenyl propamidobenzoic acid; commercially available from Symrise (Holzmiden, Germany) and SEPICALM (INCI: sodium palmitoyl proline, nymphaea alba flower extract; commercially available from Seppic (Fairfield, N.J.).

The compositions can further include a humectant. Humectants can elevate the hydration of the skin, in particular the epidermis and the dermis. Suitable humectants can be, for example, glycerol, glycerin, lactic acid, urea, aloe vera, betaine, hyaluronic acid, propanediol, propylene glycol, butylene glycol, and combinations thereof.

The compositions can further include an emulsifier, and in particular, an emulsifier that creates liquid crystalline networks or liposomal networks. Suitable non-limiting exemplary emulsifiers include, for example, OLIVEM® 1000 (INCI: Cetearyl Olivate (and) Sorbitan Olivate; commercially available from HallStar Company (Chicago, Ill.)), Arlacel™ LC (INCI: Sorbitan Stearate (and) Sorbityl Laurate; commercially available from Croda (Edison, N.J.), CRYSTALCAST® MM (INCI: Beta Sitosterol (and) Sucrose Stearate (and) Sucrose Distearate (and) Cetyl Alcohol (and) Stearyl Alcohol; commercially available from MMP Inc. (South Plainfield, N.J.), UNIOX CRISTAL (INCI: Cetearyl Alcohol (and) Polysorbate 60 (and) Cetearyl Glucoside; commercially available from Chemyunion (São Paulo, Brazil). Other suitable emulsifiers include lecithin, hydrogenated lecithin, lysolecithin, phosphatidylcholine, phospholipids, and combinations thereof.

The compositions can further include a preservative to preserve the stability. Preservatives can also prevent the growth of microbial organisms in the compositions. Suitable preservatives are known in the art, and include, for example, methylparaben, phenoxyethanol, capryl glycol, glyceryl caprylate, benzoic acid, sorbic acid, gallic acid, propylparaben and combinations thereof.

The compositions can further include a pH adjuster to control/maintain the pH of the composition within the range of skin pH. A suitable pH range of the composition can be from about 3.5 to about 6.

The compositions can further include fragrances, scents, dyes, surfactants, rheology modifiers, film formers and other components known to be useful in personal care formulations.

Methods of Use

In another aspect, the present disclosure is directed to methods of using the topical compositions to reduce skin aging of an individual's face and body.

Thus, in one aspect, the present disclosure is directed to a method for reducing signs of skin aging of the face and body in an individual in need thereof. As used herein, "skin aging" refers to increased skin wrinkling, increased appearance of fine lines, thinning skin, sagging skin, skin dryness, and skin itchiness. The method includes topically applying a composition including an *Undaria* extract to a target skin region of the individual. The target skin region can be, for example, facial skin, neck skin, breast skin, shoulder skin, chest skin, leg skin, hand skin, feet skin, and combinations thereof.

In another aspect, the present disclosure is directed to a method for reducing signs of vulvar skin aging in an individual in need thereof. As used herein, "vulvar skin aging" refers to skin wrinkling, increased appearance of fine lines, thinning skin, sagging skin, skin dryness, and skin itchiness of the skin in the vulvar region, including the vulva, labia, labia majora, labia minor, mons pubis, vulval vestibule, and combinations thereof. The method includes topically applying a composition including an *Undaria* extract to a target skin region of the individual. The target skin region can also be, for example, vulvar skin, for example, the vulva, labia, labia majora, labia minor, mons pubis, vulval vestibule, and combinations thereof.

In another aspect, the present disclosure is directed to a method for increasing adipogenesis in an individual in need thereof. The method includes topically applying a composition including an *Undaria* extract to a target skin region of the individual. The target skin region can be, for example, facial skin, neck skin, breast skin, shoulder skin, chest skin, leg skin, hand skin, feet skin, and combinations thereof. The target skin region can also be, for example, vulvar skin, for example, the vulva, labia, labia majora, labia minor, mons pubis, vulval vestibule, and combinations thereof.

In another aspect, the present disclosure is directed to a method for increasing lipogenesis in an individual in need thereof. The method includes topically applying a composition including an *Undaria* extract to a target skin region of the individual. The target skin region can be, for example, facial skin, neck skin, breast skin, shoulder skin, chest skin, leg skin, hand skin, feet skin, and combinations thereof. The target skin region can also be, for example, vulvar skin, for example, the vulva, labia, labia majora, labia minor, mons pubis, vulval vestibule and combinations thereof.

In yet another aspect, the present disclosure is directed to a method for treating vaginal vulvar atrophy in an individual in need thereof. As used herein, vulvar atrophy refers to the thinning, drying and inflammation of the tissue in and around the vulvar region. Typically, vulvar atrophy occurs after menopause, but can also develop during breast-feeding or at any other time an individual's estrogen production declines. The method comprises topically applying a composition that comprises a *Undaria* extract and a hydrophilic carrier to a vulvar skin region of the individual.

In another aspect, the present disclosure is directed to a method for reducing signs of skin aging of the face and body in an individual in need thereof. The method includes topically applying a composition including a *Bidens* extract to a target skin region of the individual. The target skin region can be, for example, facial skin, neck skin, breast skin, shoulder skin, chest skin, leg skin, hand skin, feet skin, and combinations thereof.

In another aspect, the present disclosure is directed to a method for reducing signs of vulvar skin aging in an individual in need thereof. The method includes topically applying a composition including a *Bidens* extract to a target skin region of the individual. The target skin region can be, for example, vulvar skin, for example, the vulva, labia, labia majora, labia minor, mons pubis, vulval vestibule and combinations thereof.

In another aspect, the present disclosure is directed to a method for increasing adipogenesis in an individual in need thereof. The method includes topically applying a composition including a *Bidens* extract to a target skin region of the individual. The target skin region can be, for example, facial skin, neck skin, breast skin, shoulder skin, chest skin, leg skin, hand skin, feet skin, and combinations thereof. The target skin region can also be, for example, vulvar skin, for example, the vulva, labia, labia majora, labia minor, mons pubis, vulval vestibule and combinations thereof.

In another aspect, the present disclosure is directed to a method for increasing lipogenesis in an individual in need thereof. The method includes topically applying a composition including a *Bidens* extract to a target skin region of the individual. The target skin region can be, for example, facial skin, neck skin, breast skin, shoulder skin, chest skin, leg skin, hand skin, feet skin, and combinations thereof. The target skin region can also be, for example, vulvar skin, for example, the vulva, labia, labia majora, labia minor, mons pubis, vulval vestibule and combinations thereof.

In yet another aspect, the present disclosure is directed to a method for treating vulvar atrophy in an individual in need thereof. The method comprises topically applying a composition that comprises a *Bidens* extract and a hydrophilic carrier to a vulvar skin region of the individual.

In another aspect, the present disclosure is directed to a method for reducing signs of skin aging of the face and body in an individual in need thereof. The method includes topically applying a composition including an *Undaria* extract and a *Bidens* extract to a target skin region of the individual. The target skin region can be, for example, facial skin, neck skin, breast skin, shoulder skin, chest skin, leg skin, hand skin, feet skin, and combinations thereof.

In another aspect, the present disclosure is directed to a method for reducing signs of vulvar skin aging in an individual in need thereof. The method includes topically applying a composition including an *Undaria* extract and a *Bidens* extract to a target skin region of the individual. The target skin region can be, for example, vulvar skin, for example, the vulva, labia, labia majora, labia minor, mons pubis, vulval vestibule and combinations thereof.

In another aspect, the present disclosure is directed to a method for increasing adipogenesis in an individual in need thereof. The method includes topically applying a composition including an *Undaria* extract and a *Bidens* extract to a target skin region of the individual. The target skin region can be, for example, facial skin, neck skin, breast skin, shoulder skin, chest skin, leg skin, hand skin, feet skin, and combinations thereof. The target skin region can also be, for example, vulvar skin, for example, the vulva, labia, labia majora, labia minor, mons pubis, vulval vestibule and combinations thereof.

In another aspect, the present disclosure is directed to a method for increasing lipogenesis in an individual in need thereof. The method includes topically applying a composition including an *Undaria* extract and a *Bidens* extract to a target skin region of the individual. The target skin region can be, for example, facial skin, neck skin, breast skin, shoulder skin, chest skin, leg skin, hand skin, feet skin, and combinations thereof. The target skin region can also be, for example, vulvar skin, for example, the vulva, labia, labia majora, labia minor, mons pubis, vulval vestibule and combinations thereof.

As used herein, an "individual in need" refers to an individual having skin showing visible signs of aging such as, for example, wrinkles, fine lines, thinning skin, sagging skin, skin dryness, skin itchiness, skin fragility, loss of skin elasticity, and combinations thereof. As such, in some embodiments, the methods disclosed herein are directed to a subset of the general population such that, in these embodiments, not all of the general population may benefit from the methods. Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein.

As used herein, the term "individual" refers to a male human or a female human. In certain embodiments, the individual is a postmenopausal female human.

The topical compositions used in the methods described herein can further include additional ingredients as described herein and other components known to be useful in personal care formulations.

The topical compositions can be applied to the target skin region by any suitable delivery vehicle. For example, the composition can be applied as a lotion, as a wash, as a gel, as a salve, as an ointment, as a cream, as a solid stick and as a foam. Additionally, the composition can be applied with a wipe, with mitts and gloves, using an aerosol dispenser, using a pump spray, using a trigger spray and using a squeeze bottle.

The compositions can be applied daily, every other day, every couple of days, every week, every month, and every year, as desired. The compositions can be applied multiple times per day, multiple times per week and/or multiple times per month.

In some embodiments, the compositions of the present disclosure can be used with additional skin care compositions as part of a skin care regimen. For example, in facial treatment and care, users typically use multiple products for cleansing, toning, and treating the skin of the face. Accordingly, the first product comprises a first composition typically capable of providing a first benefit to a user, and the second product comprises a second composition typically capable of providing a second benefit to a user. In the present disclosure, it should be understood that at least one of the products of the regime includes the topical composition of the present disclosure, thereby providing the benefit of reducing signs of skin aging. In some embodiments, it should be understood by one skilled in the art, that while the first product and second product can independently provide any benefit known in the art of the particular care regimen, in each particular multi-product care regimen, the first product and second product may include different compositions and thus, provide different benefits to the user.

Furthermore, as with the first product and second product of the care regimen, if more than two products are used in the multi-product care regimen, such as third, fourth, and/or fifth products (and more products if more than five products are desired), it should be recognized that the additional products should include active ingredients, each independently being capable of providing additional benefits to a user.

In an alternative embodiment, the multi-product care regime can include more than two products and can be configured such to provide a multiple day regimen. Without being limiting, in one example, the multi-product care regimen provides skin care for multiple days and, as such, a first product includes, for example, a cleansing composition, a second product includes the anti-skin aging composition of the present disclosure, a third product includes the same cleansing composition as the first product, and a fourth product includes the same anti-skin aging composition as the second product.

Without being limiting, examples of additional compositions providing skin care benefits in addition to the anti-skin aging composition of the present disclosure can include compositions for cleansing, toning, treating, moisturizing, protecting, finishing, and the like.

When the additional composition is a cleansing composition, the cleansing composition may be in any form known in the art, such as, for example, hand soaps, body soaps, body washes, shampoos, surface cleaners, dish soaps, facial cleansers, hand washes, and the like. These types of cleansing compositions typically include at least one foaming agent, such as a surfactant. Although discussed herein primarily in terms of a surfactant, it should be understood that the cleansing compositions may comprise other cleansing agents, and need not comprise a surfactant. For example, in certain embodiments, the compositions may comprise a thickener, a swellable clay, a foaming agent (which may or may not comprise a surfactant (e.g., ethoxylated skin conditioning agents, solubilizers, and derivatized silicone polymers)), and optionally a solvent or other carrier. Examples of such compositions include, for example, lotions, creams, anti-microbial compositions, and the like.

Suitable surfactants for use in the cleansing composition include anionic surfactants, amphoteric surfactants, cationic surfactants, zwitterionic surfactants, non-ionic surfactants, and combinations thereof.

Suitable anionic surfactants include, for example, alkyl sulfates, alkyl ether sulfates, alkyl aryl sulfonates, alpha-olefin sulfonates, alkali metal or ammonium salts of alkyl sulfates, alkali metal or ammonium salts of alkyl ether sulfates, alkyl phosphates, silicone phosphates, alkyl glyceryl sulfonates, alkyl sulfosuccinates, alkyl taurates, acyl taurates, alkyl sarcosinates, acyl sarcosinates, sulfoacetates, alkyl phosphate esters, mono alkyl succinates, monoalkyl maleates, sulphoacetates, acyl isethionates, alkyl carboxylates, phosphate esters, sulphosuccinates (e.g., sodium dioctylsulphosuccinate), and combinations thereof. Specific examples of anionic surfactants include sodium lauryl sulphate, sodium lauryl ether sulphate, ammonium lauryl sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauroyl isethionate, sodium N-lauryl sarcosinate, and combinations thereof.

Suitable cationic surfactants include, for example, alkyl ammonium salts, polymeric ammonium salts, alkyl pyridinium salts, aryl ammonium salts, alkyl aryl ammonium salts, silicone quaternary ammonium compounds, and combinations thereof. Specific examples of cationic surfactants include behenyltrimonium chloride, stearlkonium chloride, distearalkonium chloride, chlorohexidine diglutamate, polyhexamethylene biguanide (PHMB), cetyl pyridinium chloride, benzammonium chloride, benzalkonium chloride, and combinations thereof.

Suitable amphoteric surfactants include, for example, betaines, alkylamido betaines, sulfobetaines, N-alkyl betaines, sultaines, amphoacetates, amophodiacetates, imidazoline carboxylates, sarcosinates, acylamphoglycinates, such as cocamphocarboxyglycinates and acylamphopropionates, and combinations thereof. Specific examples of amphoteric surfactants include cocamidopropyl betaine, lauramidopropyl betaine, meadowfoamamidopropyl betaine, sodium cocoyl sarcosinate, sodium cocamphoacetate, disodium cocoamphodiacetate, ammonium cocoyl sarcosinate, sodium cocoamphopropionate, and combinations thereof.

Suitable zwitterionic surfactants include, for example, alkyl amine oxides, silicone amine oxides, and combinations thereof. Specific examples of suitable zwitterionic surfactants include, for example, 4-[N,N-di(2-hydroxyethyl)-N-octadecylammonio]-butane-1-carboxylate, 5-[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, and combinations thereof.

Suitable non-ionic surfactants include, for example, mono- and di-alkanolamides such as, for example, cocamide MEA and cocamide DEA, amine oxides, alkyl polyglucosides, ethoxylated silicones, ethoxylated alcohols, ethoxylated carboxylic acids, ethoxylated amines, ethoxylated amides, ethoxylated alkylolamides, ethoxylated alkylphenols, ethoxylated glyceryl esters, ethoxylated sorbitan esters, ethoxylated phosphate esters, glycol stearate, glyceryl stearate, and combinations thereof. It will be recognized by one skilled in the art that many of the nonionic surfactants described herein may act to improve the foaming properties of the cleansing composition of the multi-product care system, and may provide a more compact, reduced bubble size or creamy foam.

The cleansing composition may also include a thickener, which acts to thicken or increase the viscosity of the cleansing formulation. A variety of thickeners may be used in the cleansing compositions described herein. In one embodiment, the thickener may be a cellulosic thickener or gum. Examples of suitable cellulosic or gum thickeners include xanthan gum, agar, alginates, carrageenan, furcellaran, guar, cationic guar, gum arabic, gum tragacanth, karaya gum, locust bean gum, dextran, starch, modified starches, gellan gum, carboxymethylcellulose, hydroxypropylcellulose, hydroyethylcellulose, propylene glycol alginate, hydroxypropyl guar, amylopectin, cellulose gum, chitosan, modified chitosan, hydroxypropyl methylcellulose, microcrystalline cellulose, silica, fumed silica, colloidal silica, dehydroxanthan gum, non-acrylic based carbomers, and combinations thereof.

Alternately or in addition, the thickener may be an acrylic based polymer. Non-limiting examples of suitable acrylic based polymer thickeners include acrylates/C10-C30 alkyl acrylate crosspolymers, certain carbomers, acrylates copolymers, aminoacrylates copolymers, and combinations thereof. Examples of commercially available acrylic based polymer thickeners include Structure® Plus (Akzo Nobel, Pasadena, Calif.), which is an acrylates/aminoacrylates/C10-30 alkyl PEG-20 itaconate copolymer, Carbopol® Aqua SF-1 Polymer (Lubrizol Advanced Materials, Cleveland, Ohio), which is an acrylates copolymer, PEMULEN® TR-1 and TR-2 and Carbopol® ETD 2020 (available from Lubrizol Advanced Materials), which are acrylates/C10-30 alkyl acrylates crosspolymers, and the Carbopol® Ultrez series of polymers (available from Lubrizol Advanced Materials), which are carbomers.

Additional suitable agents for use in the cleansing composition may include humectants, preservatives, fragrances, chelating agents, and combinations thereof.

A skin care regime may further include a toning composition. Toning compositions provide such benefits as closing pores of a user's skin, restoring the natural pH of the skin (typically, a pH of from about 5.0 to about 5.5), removing skin impurities (e.g., dirt, oils, sebum, make-up, pollutants, and the like), hydrating the skin, and generally preparing the skin for treatment using a treatment composition, such as the anti-aging composition of the present disclosure, and/or an additional treatment composition as described below.

Generally, toning compositions for skin care include astringents, humectants, carriers, and combinations thereof. Suitable astringents include, for example, ethanol, witch hazel, rose water, alum, oatmeal, yarrow, bayberry, cold water, rubbing alcohol, astringent preparations such as silver nitrate, zinc oxide, zinc sulfate, Burow's solution, tincture of benzoin, and vegetable substances such as tannic and gallic acid, and combinations thereof. As used herein, the term "cold water" refers to water having a temperature below room temperature (approximately 25° C. (77° F.)).

Suitable humectants include, for example, glycerin, glycerin derivatives, sodium hyaluronate, betaine, amino acids, glycosaminoglycans, honey, sorbitol, glycols, polyols, sugars, hydrogenated starch hydrolysates, salts of PCA, lactic acid, lactates, and urea. A particularly preferred humectant is glycerin.

Carriers for the toning compositions can be any carrier material typically known in the cosmetic and medical arts as a basis for ointments, lotions, creams, salves, aerosols, gels, suspensions, sprays, foams, and the like, and may be used in their art-established levels. In one particular embodiment, the carrier is an aqueous carrier. In another embodiment, the carrier is an alcohol carrier. The alcohol carrier can be any suitable alcohol. One particularly preferred alcohol is ethanol.

Other suitable carriers can also be used in the toning compositions. In certain embodiments, the carriers themselves can provide the skin care benefit. Non-limiting examples of suitable carriers include emollients, sterols or sterol derivatives, natural and synthetic fats or oils, polyols, surfactants, esters, silicones, and other pharmaceutically acceptable carrier materials.

In some embodiments, the skin care regimen includes a treatment composition for treating the skin in addition to the anti-aging composition of the present disclosure. Exemplary actives for the additional treatment composition may include actives that are known to have a treating effect on the skin such as improving the evenness of skin tone and reduction of acne. More specifically, the treatment agent can be selected from the group consisting of appearance modifying agents (e.g., exfoliating agents, skin-firming agents, anti-callous agents, anti-acne agents, wound care agents, enzyme agents, scar repair agents, humectant agents), therapeutic agents, pharmaceuticals (e.g., drugs, anti-oxidants, transdermal drug delivery agents, botanical extracts, vitamins, magnets, magnetic metals, and foods), xenobiotics, skin coloration agents (e.g., tanning agents, lightening agents, and brightening agents, shine control agents and drugs), shine control agents, colorant agents, surface conditioning agents (e.g., pH adjusting agents, moisturizers, skin conditioners, exfoliation agents, shaving lubricants, anti-callous agents, anti-acne agents, anti-aging agents, wound care agents, skin lipids, enzymes, scar care agents, humectants, powders, botanical extracts, and drugs) external analgesic agents, anti-inflammatory (e.g., anti-irritant agents, anti-allergy agents, wound care agents, transdermal drug delivery, and drugs), fragrances, odor neutralizing agents, soothing agents, calming agents, botanical extracts (e.g., peppermint oil, eucalyptol, eucalyptus oil, camphor, and tea tree oil), peptides, natural and synthetic fats or oils, moisture absorbers, and combinations thereof.

In one embodiment, in addition to the compositions described above, the skin care regimen includes a finishing composition. As with the other compositions, it should be understood that the various active ingredients described herein can be used in any of the products of the multi-product care regimen without departing from the scope of the disclosure.

When included, a finishing composition comprises a finishing agent that typically delivers moisturization, skin protection, or a moisture-barrier for sealing in moisture to the user. Specifically, the finishing agent can be any moisturizing agent, skin protectant, and/or moisture-barrier enhancing agent known in the art.

Additionally, the finishing agent may be capable of providing aesthetic benefits such as skin smoothing or a powdery feel. Examples of additional suitable finishing agents include skin conditioning agents (e.g., pH adjusting agents, moisturizers, skin conditioners, exfoliation agents, shaving lubricants, skin-firming agents, anti-callous agents, anti-acne agents, anti-aging agents, anti-wrinkle agents, anti-dandruff agents, wound care agents, skin lipids, enzymes, scar care agents, humectants, powders, botanical extracts, and drugs), fragrances, botanical extracts, powders, and combinations thereof.

It should be understood that the various active ingredients can be used in any of the products of the multi-product care regimen without departing from the scope of the disclosure. The specific active ingredients of the various products will depend upon the end daily regimen desired.

It should be understood by a skilled artisan that, while skin care systems will be discussed herein, regimes using the compositions of the present disclosure can be used for various other daily regimens comprising steps to cleanse, treat, moisturize and protect the skin. It is understood that skin care regimens can combine all of these steps, some of these steps, or have multiple iterations of the same steps so as to provide desired benefits to the skin.

This written description uses examples to disclose the invention, including the best mode, and also to enable any person skilled in the art to practice the invention, including making and using the compositions and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The disclosure will be more fully understood upon consideration of the following non-limiting Examples.

Example 1

Free Fatty Acid Quantification

In this Example, free fatty acid production in cells treated with various active ingredients was quantified by measuring free fatty acids in cultured media (MesenPro RS™ medium with 200 mM of L-glutamine and 10 mg/ml of gentamycin) following cell lysis.

Human adipocyte-derived stem cells (ADSC) were treated with 1% (v/v) active ingredients for 24 hours, followed by a 2-week growth period. Following ADSC lysis and prior to gene expression analysis (described below), free fatty acids were measured fluorometrically using a free fatty acid quantification kit according to the manufacturer's instructions (Abcam; Cambridge, Mass.). Positive control cells were differentiated with STEMPRO® Adipogenesis Differentiation Kit (Invitrogen, Carlsbad, Calif.).

As shown in FIG. 1, 1% ADIPOFILL'IN™ (including propanediol, ornithine, phospholipids and glycolipids, commercially available from Lucas Meyer Cosmetics (Quebec, Canada)), 1% ECOBIDENS™, and 1% UNDARINE™ had a significant effect on the production of free fatty acids as compared to the negative control. More particularly, treatment of cells with ECOBIDENS™ resulted in 6.65 nMol/µL free fatty acids production and UNDARINE™ treatment resulted in 5.48 nMol/µL free fatty acid production. ECOSAMBA™ (commercially available as ECOSAMBA™ PRO from Chemyunion Quimica LTDA (Sorocaba, Brazil)) and KOMBUCHKA™ (commercially available from Sederma, France), however, had a minimal effect on free fatty acid production.

Example 2

Adipogenesis and Lipid/Free Fatty Acid Accumulation

In this Example, cells were exposed to active ingredients to study differentiation along the adipocyte lineage as evidenced by the lipid/free fatty acid accumulation in cells as detected by Oil Red-O staining.

Figure 2A:
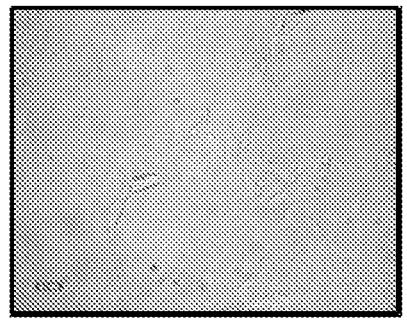
FIGS. 2A-2F are photomicrographs of mouse 3T3-L1 cells showing Oil Red-O staining after treatment of cells with various active ingredients, as discussed in Example 2.
Figure 2B:
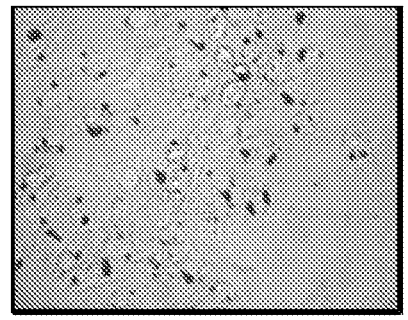
Figure 3A:
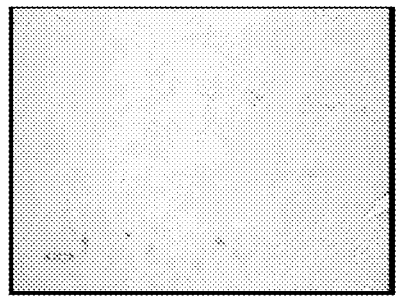
FIGS. 3A-3F are photomicrographs of human adipose derived stem cells showing Oil Red-O staining after treatment of cells with various active ingredients, as discussed in Example 2.
Figure 3B:
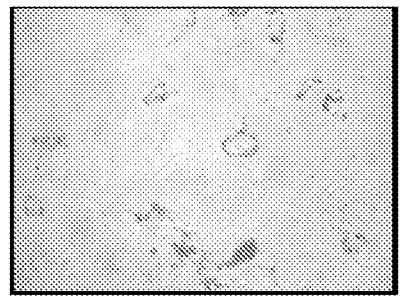

Specifically, mouse 3T3-L1 and human adipose-derived stem cells (ADSC) were exposed to 1% (v/v) active ingredients for 48 hours. Following 48 hours of exposure, standard growth media (MesenPro RS™ medium with 200 mm of L-glutamine and 10 mg/ml of gentamycin) was added and re-fed every 2-3 days to allow for differentiation along the adipose lineage for 2 weeks using the respective manufacturers' guidelines. For mouse 3T3-L1 cells, a positive control (FIG. 2B) was stimulated with DMEM (Dulbecco's Modified Eagle Medium) with 10% fetal bovine serum (FBS) and 5% penicillin/streptomycin and further supplemented with 1 µM dexamethasone, 0.5 mM IBMX and 10 µg/mL insulin. ADSC cells were differentiated with STEMPRO® Adipogenesis Differentiation Kit (Invitrogen, Carlsbad, Calif.) for a positive control (FIG. 3B).

Following 48 hours of exposure to active ingredients and the 2-week growth period, cells were fixed with 10% formalin for at least 1 hour. Formalin was removed and wells were washed with 60% isopropanol. Wells were then air dried completely. Oil Red-O working solution (filtered 0.21%) was added to each well and incubated for 10 minutes. Wells were washed under running water. Cells were imaged using a Leica DMIRB microscope at 400× magnification.

Figure 2C:
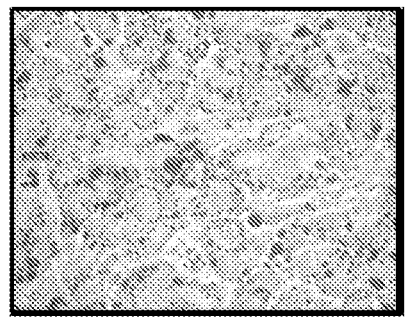
Figure 2D:
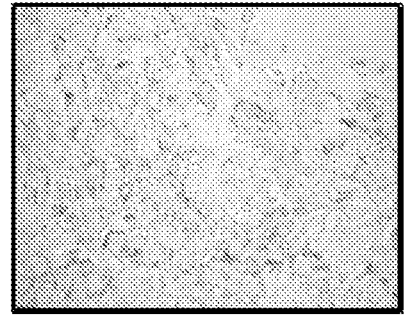
Figure 2E:
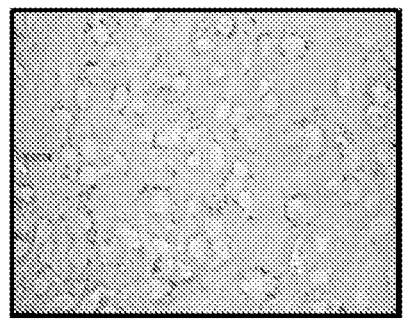
Figure 2F:
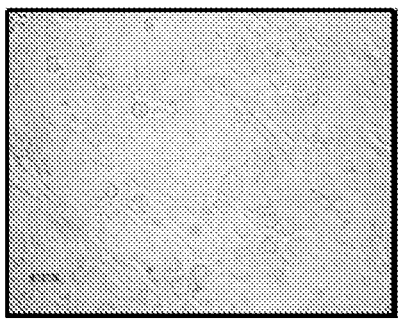
Figure 3C:
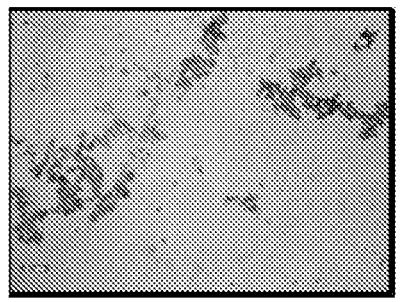
Figure 3D:
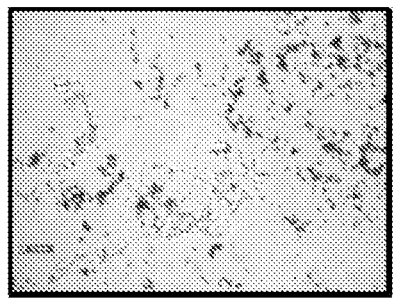
Figure 3E:
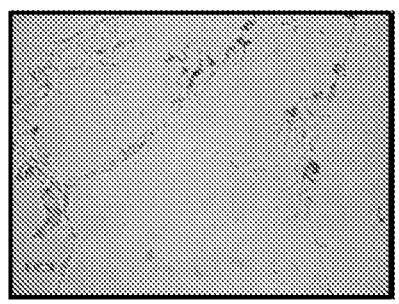
Figure 3F:
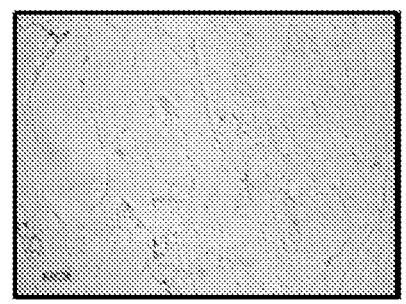

As demonstrated in FIGS. 2C and 2D, differentiated mouse 3T3-L1 cells exposed to ADIPOFILL'IN™ and ECOBIDENS™ extracts stained red (as shown, became darker in color) and became more round in shape, indicating that intracellular fatty acid content increased. Similar results were obtained in human ADSC cells (see, FIGS. 3C and 3D). Minimal staining was observed in either cell line stimulated with ECOSAMBA PRO™ or KOMBUCHKA™ (see FIGS. 2E, 2F, 3E, and 3F). Negative controls (untreated cells) were unstained and appeared elongated in shape (see, FIG. 2A and FIG. 3A). Positive controls were also stained and became more rounded in shape (see, FIG. 2B and FIG. 3B).

Example 3

Genetic Marker Analysis

In this Example, qRT-PCR was used to measure expression of genes involved in adipogenesis.

PPAR-gamma is involved in adipogenesis signaling cascades as a known adipogenesis promoter. To investigate the expression of PPAR-gamma in adipogenesis stimulation via the active ingredients, RNA was isolated from treated ADSCs for qRT-PCR analysis. Relative expression of PPAR-gamma was compared to β-Actin (a housekeeping gene) and all samples were normalized to a negative control (untreated cells). Positive control cells were differentiated with STEMPRO® Adipogenesis Differentiation Kit (Invitrogen, Carlsbad, Calif.).

RNA was isolated from differentiated cells according to the manufacturer's instructions (QIAGEN RNeasy kit). cDNA was generated using QIAGEN First Strand Reverse Transcriptase kit according to the manufacturer's directions. TaqMan 2× Universal Master Mix with TaqMan GAPDH (VIC), β-Actin (VIC), and PPAR-gamma (FAM) validated probes were used to quantify relative expression to negative control. Delta-Delta cycle threshold (ΔΔCT) method was used for comparative analysis.

Figure 4:
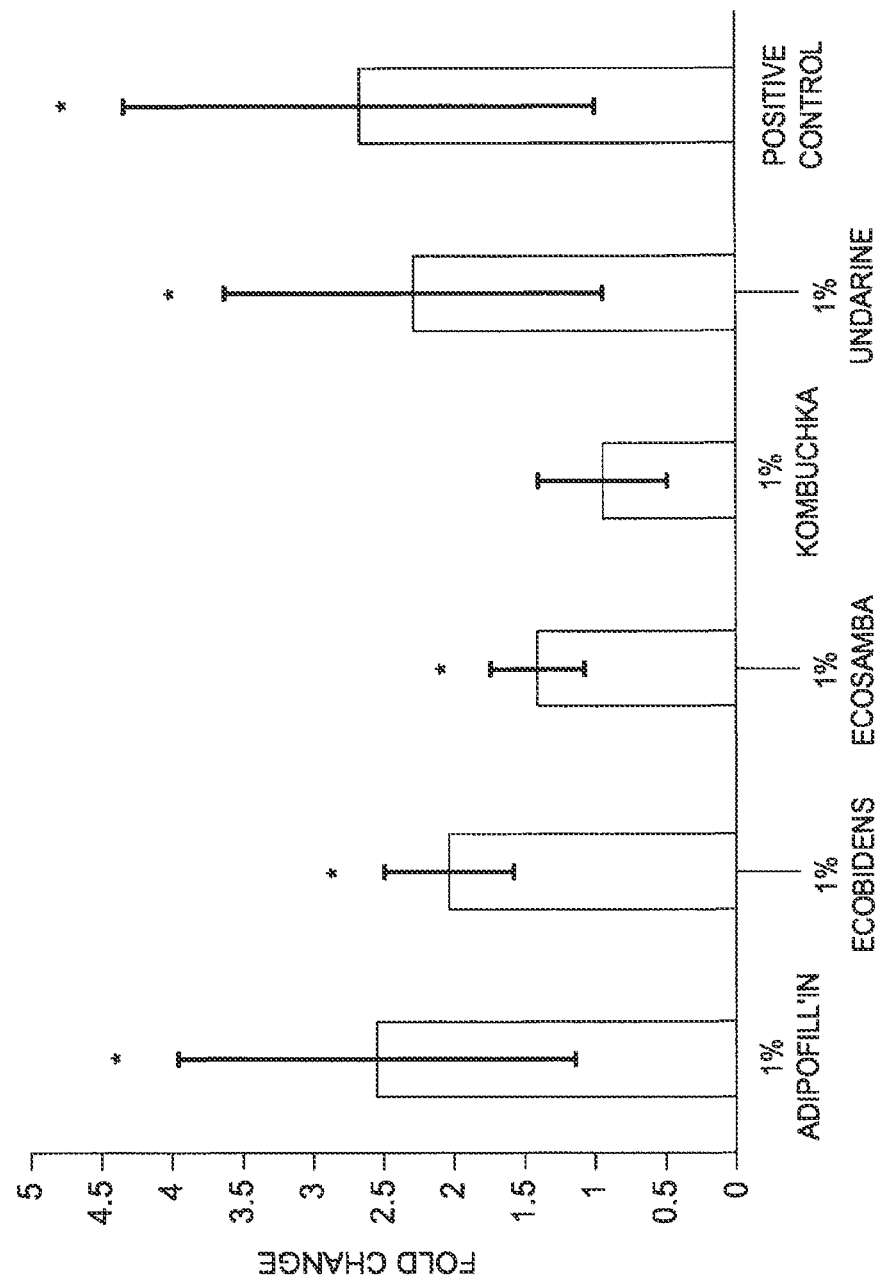
FIG. 4 is a graphical illustration showing expression of PPAR-gamma adipogenesis promoter after treatment of cells with various active ingredients, as discussed in Example 3. *$P<0.05$ by Student's T test to negative control, N=3. Data represents mean with standard deviation.

As shown in FIG. 4, a significant upregulation of PPAR-gamma was observed in cells treated with ADIPOFILL'IN™, ECOBIDENS™, ECOSAMBA™, and UNDARINE™.

Example 4

In this Example, an *Undaria* extract was tested for its effect on adipogenesis.

Specifically, *Undaria* extract (UNDARINE™) was applied to human adipose-derived stem cells (ADSC) at 1% (v/v). Cells were treated and grown as described in Example 1 above. Following exposure to UNDARINE™, ADSC were fixed with 10% formalin for at least 1 hour. Formalin was removed and wells were washed with 60% isopropanol. Wells were then air dried completely. Oil Red-O working solution (filtered 0.21%) was added to each well and incubated for 10 minutes. Wells were washed under running water. Cells were imaged using a Leica DMIRB microscope at 400× magnification.

Figure 5:
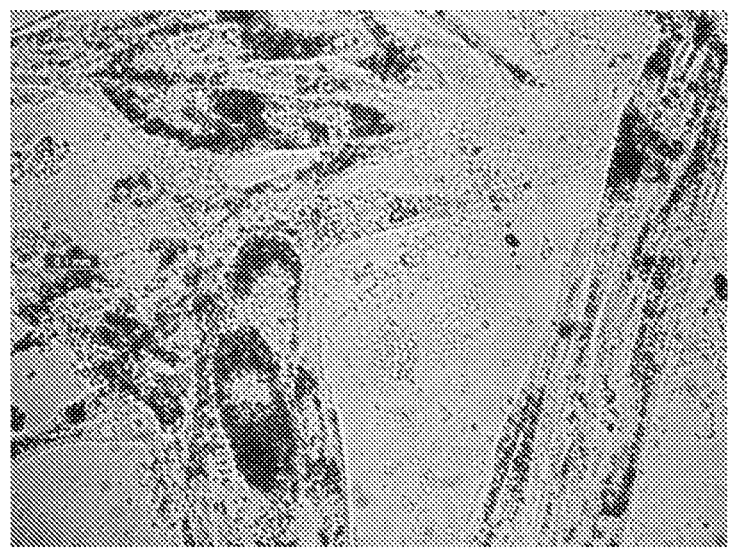
FIG. 5 is a photomicrograph of human ADSC stained red with Oil Red-0, demonstrating the production of fatty acids in response to treatment with *Undaria* extract, as discussed in Example 4.

As shown in FIG. 5, human ADSC stained red (as shown, became darker in color) with Oil Red-O, demonstrating the production of fatty acids in response to *Undaria* extract treatment.

Example 5

In this Example, standardized fucoidan *Undaria* extracts, were tested for effect on adipogenesis, and compared to the *Undaria* extracts used in the present disclosure.

Specifically, *Undaria* spp. are brown algae plants that contain fucoidan in the cell walls. Fucoidan has been shown to inhibit adipogenesis. As described in the Examples above, however, UNDARINE™ surprisingly and unexpectedly promoted adipogenesis and lipid production (see, FIGS. 1 and 5). To further examine the unexpected benefits from UNDARINE™, mouse 3T3-1L cells were treated with an *Undaria*-based extract, either UNDARINE™ or WAKAMINE® (an *Undaria pinnatifida* extract, obtained from SOLIANCE, France), or one of two standardized fucoidan *Undaria* extracts, MARITECH® REVERSE or MARITECH® GLYCOMIX (both obtained from Marinova Pty. Ltd. (Cambridge, Australia)). In particular, cells were treated with 1% (v/v) of one of: WAKAMINE®, MARITECH® REVERSE, which is purported to include 85% fucoidan, or MARITECH® GLYCOMIX, which is purposed to include 80% fucoidan, as described in Example 2.

Figure 6A:
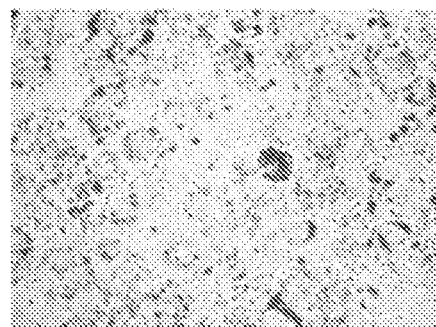
FIGS. 6A-6F are photomicrographs of mouse 3T3-1L cells stained with Oil Red-O following treatment with various extracts, as discussed in Example 5.
Figure 6B:
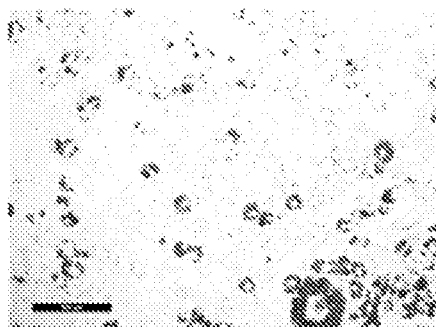
Figure 6C:
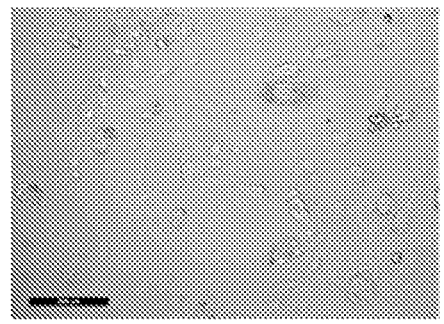
Figure 6D:
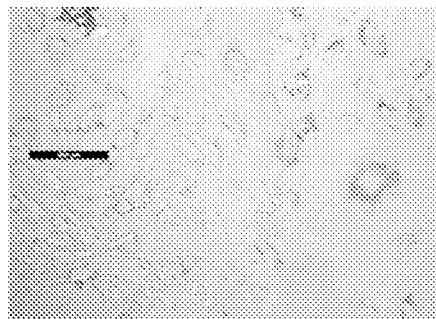
Figure 6E:
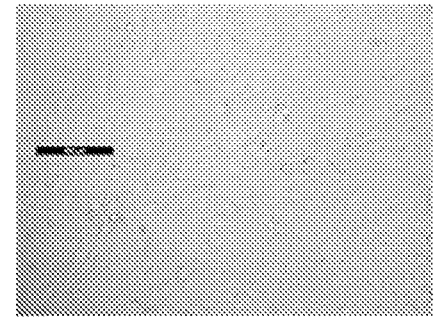
Figure 6F:
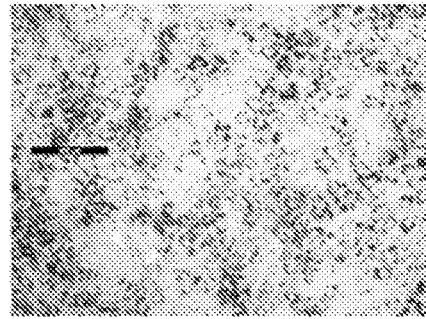

A positive control (FIG. 6F) included cells differentiated with STEMPRO® Adipogenesis Differentiation Kit (Invitrogen, Carlsbad, Calif.) and a negative control (FIG. 6E) included untreated cells. Cells were stained using Oil Red-O staining as described above.

As shown in FIGS. 6A-6F, UNDARINE™ and WAKAMINE® promoted adipogenesis (FIGS. 6A & 6B), whereas MARITECH® REVERSE and MARITECH® GLYCOMIX (FIGS. 6C & 6D) did not. This Example confirms that fucoidans do not have an adipogenesis or lipogenesis effect on cells. And, thus, it unexpectedly demonstrates that the *Undaria* extracts in the compositions of the present disclosure, provide these benefits, despite being of the same genus, which is known not to promote adipogenesis.

Example 6

In this Example, active ingredients known to stimulate adipogenesis and/or lipogenesis were tested for effect on adipogenesis and/or lipogenesis in ADSC.

Particularly, mouse 3T3-1L cells were treated with the following active ingredients known to stimulate adipogenesis and/or lipogenesis: 1% (w/v) SYM3D™ (commercially available from Symrise, Teterboro, N.J.), 1% (w/v) VOLU-FILINE™ (commercially available from Sederma, France), 1% (w/v) COMMIPHEROLINE™ (commercially available from Soliance, France), 1% (w/v) BIO-BUSTYL™ (commercially available from Sederma, France), 1% (w/v) CEL-LACTIVE® FORM (commercially available from Rahn, USA Corp., Aurora, Ill.), 1% (w/v) ADIFYLINE® (commercially available from Lipotec, Spain), and 1% (w/v) VOLUFORM™ (commercially available from SEPPIC, France). More particularly, these active ingredients have been previously marketed for increasing breast size and/or plumping the neck/chest area via adipogenesis and/or lipogenesis. Cells were stained using Oil Red-O staining as described above.

As shown in FIGS. 7A-7G, some of these actives did not show adipogenesis/lipogenesis activity at all. And further, as compared to FIGS. 5 and 8A-8D, UNDARINE™, as well as the various *Bidens* extracts, performed as well or better in stimulating adipogenesis and/or lipogenesis as compared to the known active ingredients.

Example 7

In this Example, *Bidens*-based extracts were tested for their effects on adipogenesis.

Figure 8A:
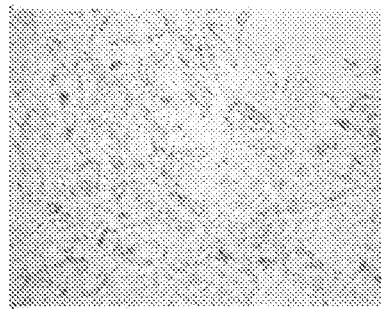
FIGS. 8A-8F are photomicrographs of mouse 3T3-1L cells stained red with Oil Red-O following treatment with various *Bidens* extracts, as discussed in Example 7.
Figure 8B:
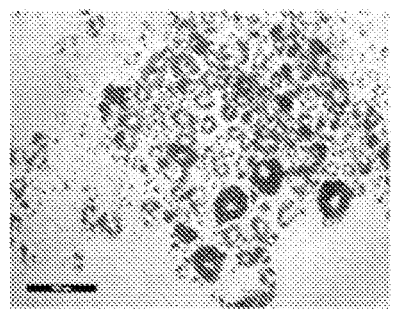
Figure 8C:
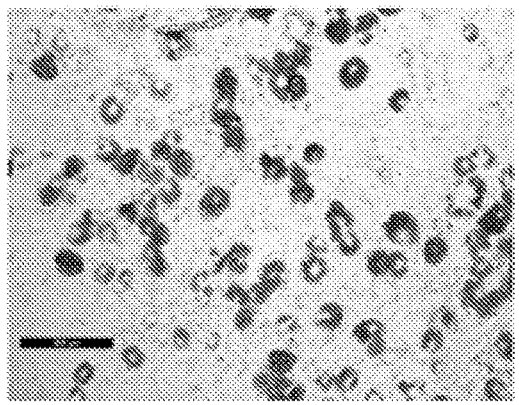
Figure 8D:
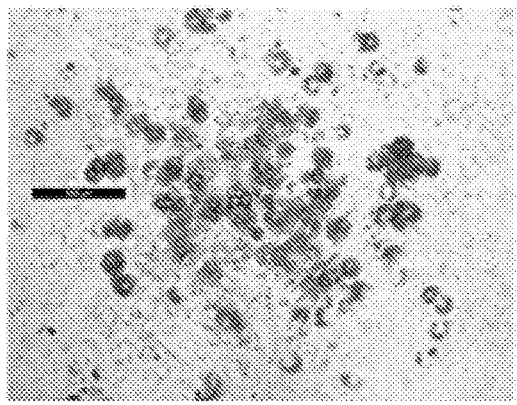
Figure 8E:
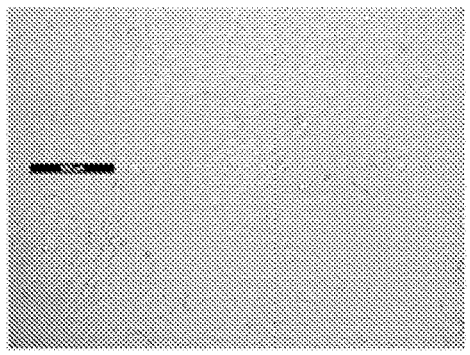
Figure 8F:
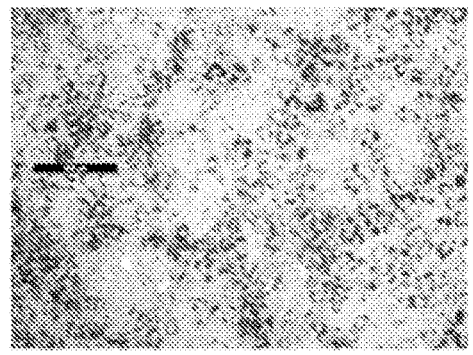

Specifically, *Bidens pilosa* extract (ECOBIDENS™, obtained from Chemyunion), *Bidens bipinnata* extract (obtained from Carrubba), *Bidens pilosa* extract (obtained from Carrubba), and *Bidens tripartita* extract (Provital Water Agrimony Extract H.G., obtained from Provital Group, Spain) were applied to mouse 3T3-1L cells at 1% (v/v). Cells were treated and grown as described above and analyzed by Oil Red O staining. A positive control (FIG. 8F) included mouse 3T3-1L cells stimulated with DMEM supplemented with 1 μM dexamethasone, 0.5 mM IBMX and 10 μg/mL insulin and a negative control (FIG. 8E) included untreated cells.

As shown in FIGS. 8A-8D mouse 3T3-1L cells stained red with Oil Red-O, demonstrating the production of fatty acids in response to the various *Bidens* extracts.

Example 8

In this Example, active ingredients were tested for effect on cell proliferation.

Specifically, human dermal fibroblasts were stained with carboxyfluorescein succinimidyl ester (CFSE) prior to treatment with ADIPOFILL'IN™, ECOBIDENS™, ECOSAMBA PRO™, KOMBUCHKA™, UNDARINE™ or the combination of ADIPOFILL'IN™/ECOSAMBA PRO™. To establish a proliferation index, cells were measured at 0 hour, 24 hours, 48 hours and 96 hours.

Figure 9:
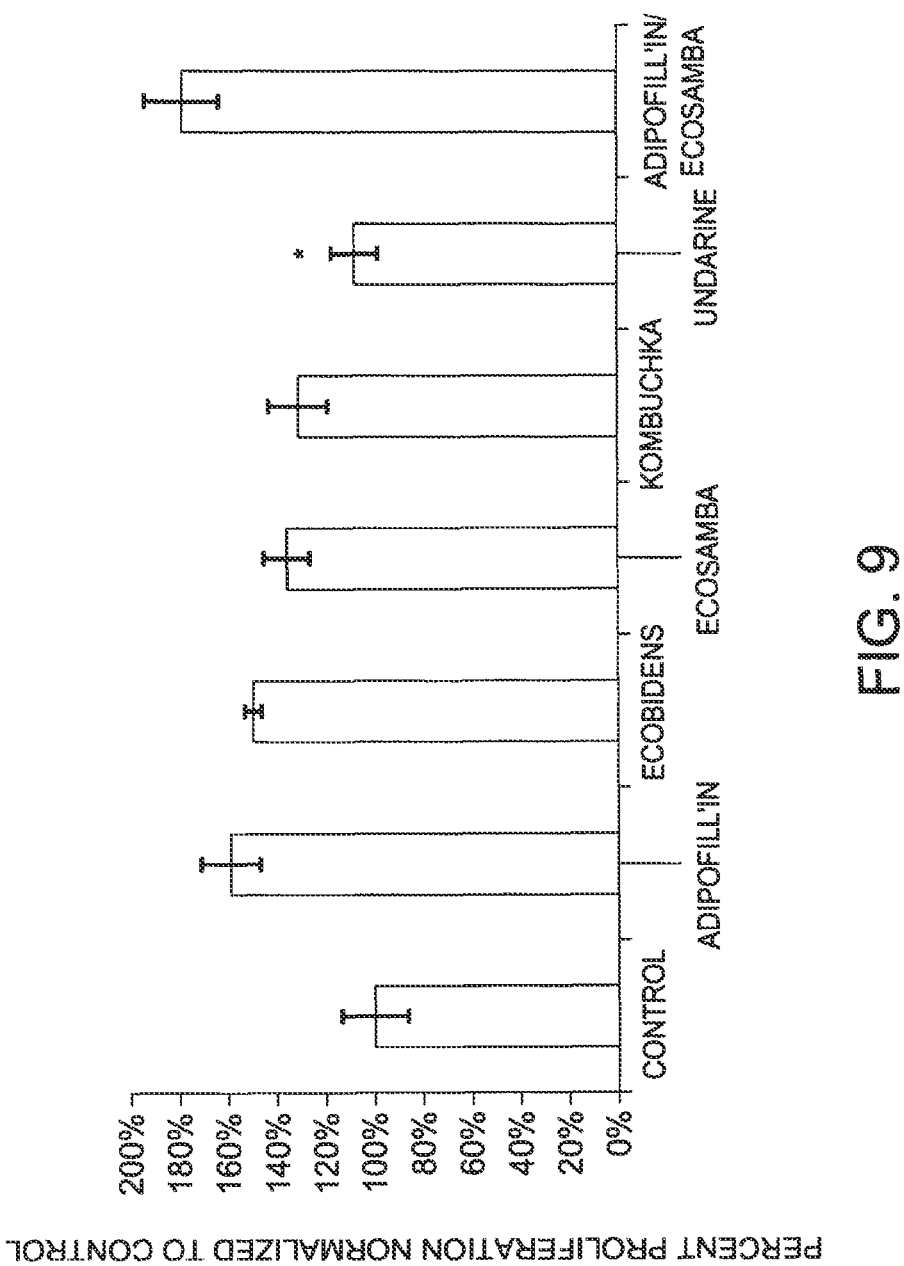
FIG. 9 is a graphical illustration showing percent cellular proliferation of human dermal fibroblasts following treatment with various active components, as discussed in Example 8.

As shown in FIG. 9, all of the actives except UNDARINE™ induced significantly greater cellular proliferation as compared to a control (untreated cells). Further, the combination of ADIPOFILL'IN™/ECOSAMBA PRO™ resulted in the greatest increase in fibroblast proliferation (see, FIG. 9) showing that this combination provides this additional benefit.

With respect to the sample treated with UNDARINE™, it is believed that the increased proliferation of fibroblasts involves a separate cellular pathway from adipogenesis and/or lipogenesis involving adipocytes. That is, this Example demonstrates that some of these active ingredients can affect a fibroblast-based pathway, which is separate from the pathway involving adipocytes.

Example 9

In this Example, microarray analysis was conducted on human ADSCs to compare effects of *Undaria* and *Bidens* extracts on gene expression.

In particular, human ADSCs were treated with 1% (v/v) *Undaria* extract, UNDARINE™, or *Bidens* extract, ECO-BIDENS™, as described in Example 1 above for 48 hours and then allowed to differentiate in standard growth media for two weeks. After two weeks, the RNA samples were collected from the extract-treated cells and untreated control cells and submitted to a commercial service provider for microarray analysis using HEEBO human chips (Ocean Ridge Biosciences, Palm Beach Gardens, Fla.).

Fold changes in expression were calculated for each treatment relative to untreated controls (i.e., *Undaria* treated/untreated and *Bidens* treated/untreated). Fold changes were analyzed in Genesis (Release 1.7.5) using 2D hierarchical clustering. The fold change data (p-value<0.05, false discover rate (FDR)<=0.1, fold change>2) was log 2 transformed prior to clustering. 2D hierarchical clustering was performed using Euclidean distance and average linkage for the different genes and the treatments. Results were demonstrated using a heat map where green indicated decreased expression and red indicated increased expression relative to untreated controls (not shown).

Cluster analysis of the microarray showed changes in gene regulation in both *Undaria*- and *Bidens*-treated cells as compared to the untreated control sample (not shown). Table 1 provides a list of genes that responded to treatment in which "No Threshold" genes represented those that were up or down regulated (but, by less than 2-fold) and different result between *Undaria* and *Bidens* treatments. "Threshold" genes represented those that were significantly up or down regulated (by a factor greater than 2-fold) and different result between *Undaria* and *Bidens* treatments. The microarray analysis demonstrated that *Undaria* and *Bidens* treatment induces changes in gene expression.

TABLE 1

| Gene | Gene Name | Bidens | Undaria |
|---|---|---|---|
| No Threshold (less stringent) | | | |
| CEP57.RP11-296o14.2 | centrosomal protein, Translokin | down-regulated | down-regulated |
| CYP1B1 | Cytochrome P450 (lipid synthesis) | up-regulated | down-regulated |
| KANK4 | KN motif and ankyrin repeat domain | up-regulated | down-regulated |
| GCLM | Glutamate-Cysteine Ligase | up-regulated | down-regulated |
| NRCAM | Neuronal Cell Adhesion Molecule | up-regulated | down-regulated |
| GSTM3 | glutathione S-transferase M | up-regulated | down-regulated |
| LIPG | Endothelial Lipase | up-regulated | down-regulated |
| RCAN1 | Regulator of Calcineurin | up-regulated | down-regulated |
| EIF2AK2 | Eukaryotic Translation Initiation Factor 2- Alpha Kinase | up-regulated | down-regulated |
| KCNE4 | Potassium voltage-gated channel subfamily E | up-regulated | down-regulated |
| FAM107B | Family With Sequence Similarity 107 | up-regulated | down-regulated |
| HIF1A | Hypoxia-inducible factor 1-alpha | up-regulated | down-regulated |
| KRT6A | Keratin type II | up-regulated | down-regulated |
| RBM26 | RNA binding motif-26 | down-regulated | down-regulated |
| MMRN2 | elastin microfibril interfacer 3 | down-regulated | down-regulated |
| GMPR | Guanosine Monophosphate Reductase | down-regulated | up-regulated |
| CAMK2D | Calcium/Calmodulin-Dependent Protein Kinase II Delta | down-regulated | up-regulated |
| ACTG2 | Actin Gamma II | down-regulated | up-regulated |
| CAMPK1G | Calcium/Calmodulin-Dependent Protein Kinase I Gamma | down-regulated | up-regulated |
| TNPO2 | Transportin II, nuclear transport receptor | down-regulated | up-regulated |
| RP11-341GS.3 | unknown | down-regulated | up-regulated |
| KRT15 | Keratin type 115 | up-regulated | up-regulated |
| CEP170 | centrosomal protein | down-regulated | up-regulated |
| CASP1 | Caspase 1 precursor | down-regulated | up-regulated |
| THRESHOLD | | | |
| CYGB | Cytoglobin tumor suppressor | up-regulated | up-regulated |
| GALNTL4 | galactosamine:polypeptide N-acetylgalactosaminyltransferase-like 4. | up-regulated | up-regulated |
| KRT13 | Keratin type 13 | up-regulated | down-regulated |
| KRT6A | Keratin type II | up-regulated | down-regulated |
| ERVWE1 | Syncytin envelope gene | up-regulated | down-regulated |
| CYP1B1 | Cytochrome P450 (lipid synthesis) | up-regulated | down-regulated |
| KANK4 | KN motif and ankyrin repeat domain | up-regulated | down-regulated |
| F3 | coagulase factor III | up-regulated | down-regulated |
| GCLM | glutamate-cysteine ligase | up-regulated | down-regulated |
| GSTM3 | glutathione S-transferase M | up-regulated | down-regulated |
| NRCAM | Neuronal cell adhesion molecule | up-regulated | down-regulated |
| PPM1A | protein phosphatase, Mg2+/Mn2+ dependent | up-regulated | down-regulated |
| UBE2K | ubiquitin-conjugating enzyme | up-regulated | down-regulated |
| SPRY4 | mitogen-activated protein kinase inhibitor | up-regulated | down-regulated |
| FNTAP1 | farnesyltransferase | up-regulated | down-regulated |
| NDNL2 | necdin-like 2 | up-regulated | down-regulated |
| MMRN2 | elastin microfibril interfacer 3 | down-regulated | down-regulated |
| CAMK2D | Calcium/Calmodulin-Dependent Protein Kinase II Delta | down-regulated | up-regulated |
| CEP 170 | centrosomal protein | down-regulated | up-regulated |
| CCL11 | C-C motif chemokine 11 | down-regulated | up-regulated |
| GBP2 | guanylate binding protein 2, | down-regulated | up-regulated |

Example 10

Cell Survival

In this Example, a cell survival test was conducted to test for cytotoxicity of active ingredients.

Specifically, human dermal fibroblasts (HDFs) were exposed for 24 hours to growth media (DMEM+10% FBS) containing 0.5, 1, 2 and 5% v/v of active ingredients. After 24 hours exposure, MTT solution (thiazolyl blue tetrazolium blue) was added to cell culture wells for 2-4 hours at 37° C. MTT solution was then removed and isopropyl alcohol was added and incubated overnight at room temperature in the dark. Wells were measured at OD570 and compared to untreated control cells to determine cell survival.

Figure 10:
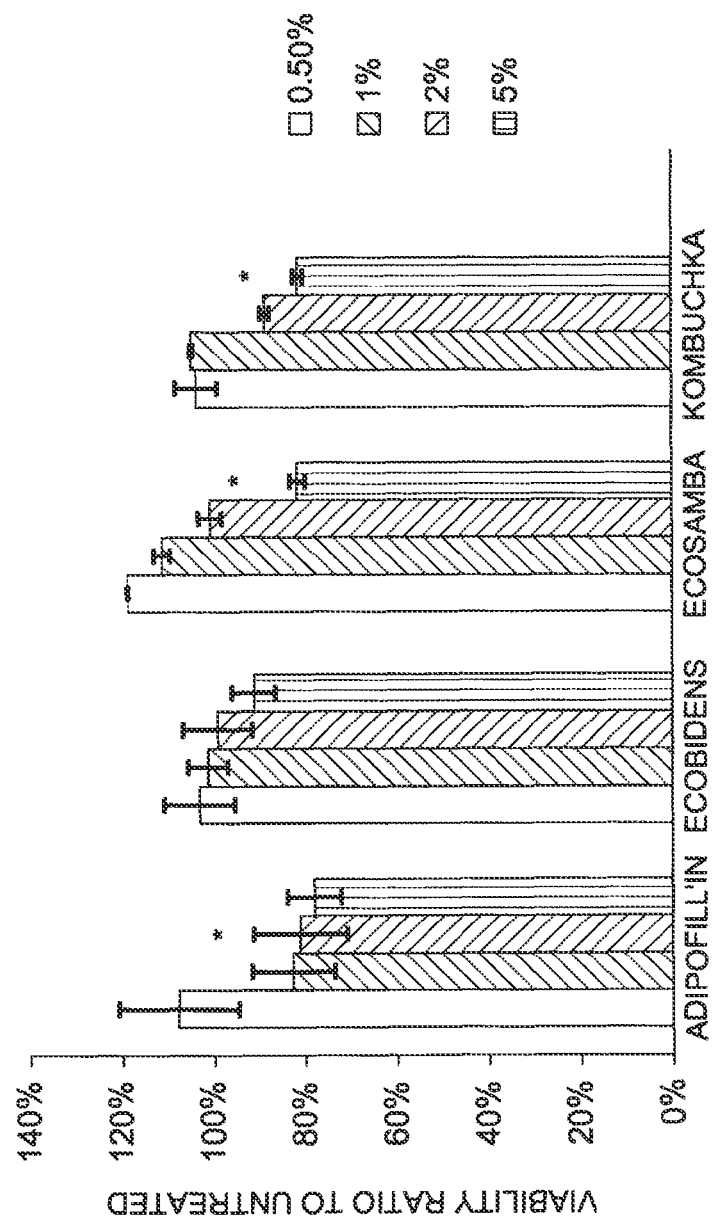
FIG. 10 is a graphical illustration showing cell survival following treatment of cells with various active ingredients, as discussed in Example 10.

As demonstrated in FIG. 10, none of the tested active ingredients significantly reduced cellular survival, nor did any significantly produce IL1-alpha, pro-inflammatory cytokine.

Example 11

In these Examples, exemplary topical compositions were prepared with the following components:

TABLE 2

| Gel formulation | | | |
|---|---|---|---|
| Trade Name | INCI | Wt % | Function |
| A | | | |
| Water | Water | 67.49 | Carrier |
| Carbopol Ultrez 21 | Carbomer | 1 | Hydrophilic Thickener |
| Disodium EDTA | Disodium EDTA | 0.01 | |
| Sodium Hydroxide | Sodium Hydroxide (10%) | q.a to pH 6.0 | |
| B | | | |
| SDA 40B Ethanol | Alcohol | 20 | Polar Co-Solvent |
| Polyderm PPI-G7/CA | Glycereth-7-Diglycerol-PEG-15 Cocamine/IPDI Copolymer | 0.5 | |
| UNDARINE ™ | Glycerine, Water, Algae (*Undaria pinnatifida*) Extract | 2 | Active |
| ECOBIDENS ™ | Water, Glycerin, *Bidens pilosa* Extract | 5 | Active |
| Glycerin | Glycerin | 2 | Carrier |
| Propylene Glycol | Propylene Glycol | 2 | Penetration Enhancer |
| TOTAL | | 100 | |

TABLE 3

| Oil-Free Serum Formulation | | | |
|---|---|---|---|
| Trade Name | INCI Name | Wt. % | Function |
| Water | Water | 85.4 | Carrier |
| Structure Solanace | Potato Starch Modified | 3 | Hydrophilic Thickener |
| Simulgreen | Hydroxystearyl Alcohol, Hydroxystearyl Glucoside | 1 | |
| NaOH 10% | Sodium Hydroxide | q.s | |
| Zemea | Propanediol | 1 | Polar Co-Solvent |
| ECOBIDENS ™ | Water, Glycerin, *Bidens Pilosa* Extract | 2 | Active |
| UNDARINE ™ | Glycerine, Water, Algae (*Undaria pinnatifida*) Extract | 2 | Active |
| Arlasolv DMI | Dimethyl Isosorbide | 0.5 | Penetration Enhancer |
| Floraesters K-20W Jojoba | Hydrolyzed Jojoba Esters, Water | 0.5 | |
| SymDiol 68 | 1,2-Hexanediol, Caprylyl Glycol | 1 | |
| Glycerox 767 | PEG-6 Caprylic/Capric Glycerides | 1.5 | |
| Fragrance | Fragrance | 0.1 | |
| DryFlo Elite LL | Aluminum Starch Octenylsuccinate and Lauroyl Lysine | 2 | |
| Total: | | 100 | |

TABLE 4

| Oil in Water Emulsion | | | |
|---|---|---|---|
| Product A | INCI | Wt % | Function |
| Water | Water/Aqua | 77.85 | Carrier |
| Arlasolve DMI | Dimethyl Isosorbide | 1 | Penetration Enhancer |
| Transcutol CG | Ethoxydiglycol | 1 | Polar Co-Solvent |
| Structure Solanace | Potato Starch Modified | 3 | Hydrophilic Thickener |
| Product B | | | |
| Olivem 1000 | Cetearyl Olivate, Sorbitan Olivate | 1 | |
| Velsan SC | Sorbitan Caprylate | 0.5 | |
| Silwax D226 | Cerotyl Dimethicone | 1 | |
| Behenyl Alcohol | Behenyl Alcohol | 1 | |
| Dermol 99 | Isononyl Isononanoate | 2 | |
| Crodamol STS | PPG-3 Benzyl Ether Myristate | 1.5 | |
| Tegosoft M | Isopropyl Myristate | 0.75 | |
| Stimutex | Spent Grain Wax, Triolein, Linoleic Acid, Triticum Vulgare (Wheat) Germ Oil, Palmitic Acid Behenic Acid, Beta-Sitosterol | 0.25 | |
| BHT | BHT | 0.05 | |
| Sitosterol 75 MM | B-Sitosterol | 0.1 | Active |
| Product C | | | |
| Xiameter 200 100cst | Dimethicone | 1 | |
| UNDARINE ™ | Glycerine, Water, Algae (*Undaria pinnatifida*) Extract | 2 | Active |
| Geogard ECT | Benzyl Alcohol & Salicylic Acid & Glycerin & Sorbic Acid | 1 | |

TABLE 4-continued

Oil in Water Emulsion

| Product A | INCI | Wt % | Function |
|---|---|---|---|
| ECOBIDENS ™ | Water, Glycerin, *Bidens pilosa* Extract | 5 | Active |
| Citric Acid | Citric Acid | q.a. to pH 5.5 | |
| Sodium Hydroxide | Sodium Hydroxide | q.a. to pH 5.5 | |

TABLE 5

Foaming Body Wash

| Trade Name | INCI Name | % Wt. | Function |
|---|---|---|---|
| Part A | | | |
| Water | Water/Aqua | 90.919 | Carrier |
| Tic Prehydrated Xanthan Gum | Xanthan Gum | 0.050 | Hydrophilic Thickener |
| Versene NA2 | Disodium EDTA | 0.100 | |
| Aloe Vera Powder 200x | Aloe Baradensis Leaf Juice | 0.010 | |
| L-Panthenol | Panthenol | 0.100 | |
| Sodium Benzoate, FCC | Sodium Benzoate | 0.450 | |
| Zemea prorandiol | 1,2-Propanediol | 1.500 | Polar Co-solvent |
| Glycerin, 99.7% | Glycerin | 1.000 | Penetration Enhancer |
| Mackam 35 UL HA | Cocamidopropyl Betaine | 3.000 | |
| Plantacare 2000 N UP | Decyl Glucoside | 1.000 | |
| Part B | | | |
| Sensiva SC 50 | Ethylhexylglycerine | 0.300 | |
| Tagat CH 60 | PEG-60 Hydrogenated Caster Oil | 0.750 | |
| Alkumuls SML 20 | Polysorbate 20 | 0.45 | |
| Sistosterol 75 MM | Beta-Sistosterol | 0.0015 | Active |
| Part C | | | |
| ECOBIDENS ™ | Water, Glycerin, *Bidens pilosa* Extract | 0.100 | Active |
| UNDARINE ™ P | Glycerine, Water, Algae (*Undaria pinnatifida*) Extract | 0.100 | Active |
| US260085/00 (Aloe Fresh) | Fragrance | 0.100 | |
| 50% Citric Acid | Citric Acid, Water | 0.070 | |
| | Total | 100.000 | |

These results further indicate that topical compositions including an *Undaria* extract, topical compositions including a *Bidens* extract, and topical compositions including an *Undaria* extract and a *Bidens* extract can improve the overall fullness and appearance of aging skin by increasing adipocyte number and adipocyte lipid/free fatty acid production. The compositions and methods can improve the appearance of aging skin of the face, neck and body. The compositions and methods can also improve the appearance of skin of the vulva and the labia, particularly in postmenopausal women.

What is claimed is:

1. A topical composition comprising: an active ingredient, a hydrophilic carrier and a skin penetration enhancer, wherein the active ingredient consists essentially of an *Undaria* extract and a *Bidens* extract and optionally, beta-sitosterol, and wherein the *Undaria* extract is present in an amount of from about 0.1% (w/w) to about 5% (w/w) and the *Bidens* extract is present in an amount of from about 0.1% (w/w) to about 5% (w/w).

2. The topical composition of claim 1 wherein the *Undaria* extract is selected from the group consisting of *Undaria crenata*, *Undaria peterseniana*, *Undaria pinnatifida*, *Undaria undarioides*, and combinations thereof.

3. The topical composition of claim 1 wherein the hydrophilic carrier is selected from the group consisting of water, alcohol, glycerin, glycerin derivatives, glycol, water-soluble emollients, and combinations thereof.

4. The topical composition of claim 1 wherein the *Bidens* extract is selected from the group consisting of *Bidens alba*, *Bidens amplectens*, *Bidens amplissima*, *Bidens aristosa*, *Bidens asymmetrica*, *Bidens aurea*, *Bidens beckii*, *Bidens bidentoides*, *Bidens bigelovii*, *Bidens bipinnata*, *Bidens biternata*, *Bidens campylotheca*, *Bidens cernua*, *Bidens cervicata*, *Bidens chippii*, *Bidens conjuncts*, *Bidens connata*, *Bidens coronata*, *Bidens cosmoides*, *Bidens cynapiifolia*, *Bidens discoidea*, *Bidens eatonii*, *Bidens ferulifolia*, *Bidens forbesii*, *Bidens frondosa*, *Bidens gardneri*, *Bidens hawaiensis*, *Bidens henryi*, *Bidens heterodoxa*, *Bidens heterosperma*, *Bidens hillebrandiana*, *Bidens hyperborean*, *Bidens laevis*, *Bidens lemmonii*, *Bidens leptocephala*, *Bidens leptophylla*, *Bidens macrocarpa*, *Bidens mannii*, *Bidens mauiensis*, *Bidens maximowicziana*, *Bidens menziesii*, *Bidens micrantha*, *Bidens mitis*, *Bidens molokaiensis*, *Bidens x multticeps*, *Bidens parviflora*, *Bidens pilosa*, *Bidens polylepis*, *Bidens populifolia*, *Bidens radiate*, *Bidens reptans*, *Bidens sandvicensis*, *Bidens schimperi*, *Bidens simplicifolia*, *Bidens socorrensis*, *Bidens squarrosa*, *Bidens subalternans*, *Bidens tenuisecta*, *Bidens torts*, *Bidens trichosperma*, *Bidens tripartita*, *Bidens triplinervia*, *Bidens valida*, *Bidens vulgata*, *Bidens wiebkei*, and combinations thereof.

5. The topical composition of claim 1 further comprising beta-sitosterol.

6. The topical composition of claim 5 wherein the composition comprises from about 0.001% (by weight of the composition) to about 10% (by weight of the composition) of beta-sitosterol.

7. The topical composition of claim 1, wherein the skin penetration enhancer is selected from the group consisting of sulfoxides, alcohols, fatty acids, fatty acid esters, polyols, amides, surfactants, terpenes, alkanones, organic acids, and combinations thereof.

8. A topical composition comprising an active ingredient, a skin penetration enhancer and a hydrophilic carrier, wherein the active ingredient consists essentially of an *Undaria* extract and a *Bidens* extract and optionally, beta-sitosterol, and wherein the *Undaria* extract is present in an amount of from about 0.1% (w/w) to about 5% (w/w) and the *Bidens* extract is present in an amount of from about 0.1% (w/w) to about 5% (w/w) and wherein the *Bidens* extract is selected from the group consisting of *Bidens pilosa* extract, *Bidens bipinnata* extract, *Bidens tripartita* extract and combinations thereof.

9. The topical composition of claim 8 wherein the hydrophilic carrier is selected from the group consisting of water, alcohols, glycerin, glycerin derivatives, glycols, water-soluble emollients, and combinations thereof.

10. The topical composition of claim 8 wherein the *Undaria* extract is selected from the group consisting of *Undaria crenata, Undaria peterseniana, Undaria pinnatifida, Undaria undarioides*, and combinations thereof.

11. The topical composition of claim 8 wherein the skin penetration enhancer is selected from the group consisting of sulfoxides, alcohols, fatty acids, fatty acid esters, polyols, amides, surfactants, terpenes, alkanones, organic acids, and combinations thereof.

12. The topical composition of claim 8 wherein the skin penetration enhancer is present in the composition in an amount of from about 0.01% (by weight of the composition) to about 25% (by weight of the composition).

13. The topical composition of claim 8 further comprising beta-sitosterol.

14. The topical composition of claim 8 wherein the composition comprises from about 0.001% (by weight of the composition) to about 10% (by weight of the composition) of beta-sitosterol.

15. A topical composition comprising an active ingredient, glycerin, a hydrophilic carrier and a polar co-solvent, wherein the active ingredient consists essentially of an *Undaria* extract and a *Bidens* extract and optionally, beta-sitosterol, and wherein the *Undaria* extract is present in an amount of from about 0.1% (w/w) to about 5% (w/w) and the *Bidens* extract is present in an amount of from about 0.1% (w/w) to about 5% (w/w).

16. The topical composition of claim 1 wherein the hydrophilic carrier is selected from the group consisting of glycerin, water, a glycol, and combinations thereof; and the composition further comprises a skin penetration enhancer, wherein the skin penetration enhancer is a glycol.

17. The topical composition of claim 8 wherein the hydrophilic carrier is selected from the group consisting of glycerin, water, a glycol, and combinations thereof; and the skin penetration enhancer is a glycol.

18. The topical composition of claim 1 comprising from about 1% (w/w) to about 5% (w/w) of the *Undaria* extract and from about 1% (w/w) to about 5% (w/w) of the *Bidens* extract.

19. The topical composition of claim 8 comprising from about 1% (w/w) to about 5% (w/w) of the *Undaria* extract and from about 1% (w/w) to about 5% (w/w) of the *Bidens* extract.

20. The topical composition of claim 1 further comprising a polar co-solvent.

* * * * *